(12) United States Patent
Nef

(10) Patent No.: US 7,230,155 B2
(45) Date of Patent: Jun. 12, 2007

(54) METHOD FOR IDENTIFYING AN AGONIST OF NEURONAL CALCIUM SENSOR-1 (NCS-1), FOR THERAPY OF CNS DISORDERS

(75) Inventor: Patrick Nef, Riehen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 209 days.

(21) Appl. No.: 10/124,334

(22) Filed: Apr. 17, 2002

(65) Prior Publication Data
US 2003/0159158 A1 Aug. 21, 2003

(30) Foreign Application Priority Data
Apr. 17, 2001 (EP) .................................. 01109536
Oct. 29, 2001 (EP) .................................. 01125816

(51) Int. Cl.
*G01N 33/00* (2006.01)
*A01K 67/00* (2006.01)
*A01K 67/033* (2006.01)
*A01K 67/027* (2006.01)

(52) U.S. Cl. .............................. 800/3; 800/13; 800/18
(58) Field of Classification Search .................... 800/3, 800/13, 18; 424/9.1, 9.2; 435/4
See application file for complete search history.

(56) References Cited

U.S. PATENT DOCUMENTS

| | | | |
|---|---|---|---|
| 5,624,902 A | 4/1997 | Blondelle et al. | |
| 5,981,279 A | 11/1999 | Weiss | |
| 6,165,709 A | 12/2000 | Friend et al. | |

FOREIGN PATENT DOCUMENTS

| | | |
|---|---|---|
| EP | 0 627 219 | 12/1994 |
| WO | WO 98/18947 | 5/1998 |
| WO | WO 99/61008 | 12/1999 |
| WO | WO 99/61609 A1 | 12/1999 |
| WO | WO 01/34562 A1 | 5/2001 |

OTHER PUBLICATIONS

Nicolas C. Schaad et al., *Proc. Natl. Acad. Sci.*, vol. 93, pp. 9253-9258 (1996).

(Continued)

*Primary Examiner*—Anne-Marie Falk
(74) *Attorney, Agent, or Firm*—George W. Johnston; Patricia S. Rocha-Tramaloni; Kimberly J. Prior

(57) ABSTRACT

Provided is a method for determining whether an agent is an agonist of the neuron-specific calcium sensor-1 (NCS-1), for consideration of an agonist of NCS-1 as a drug candidate for therapy of a behavioral disorder or for improving learning and/or memory of a subject, said method comprising the steps of:
(a) contacting a cell, tissue or non-human animal with an agent to be screened under conditions to permit neuron-specific calcium sensor-1 (NCS-1) activity; and
(b) determining NCS-1 activity of said treated cell, tissue or non-human animal, wherein an increase in NCS-1 activity compared with a corresponding control cell, tissue or animal is indicative of an agent which is an agonist of NCS-1.

5 Claims, 15 Drawing Sheets

Figure 1:
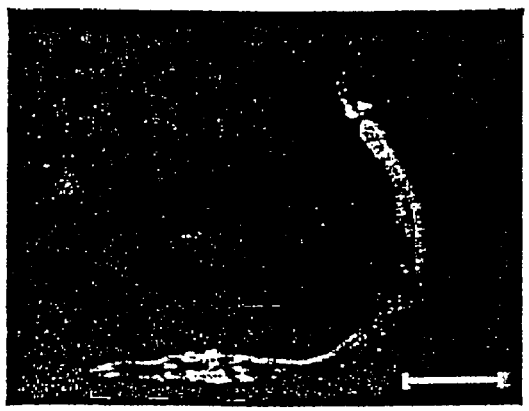
Figure 1:

A.

B.

OTHER PUBLICATIONS

*Derwent Abstract AN 2001-398934* (Mar. 14, 2001).
D. Angaut-Petit et al., *Eur. J. of Neuroscience*, vol. 10, pp. 423-434 (1998).
O. Pongs et al., *Neuron*, vol. 11, pp. 15-28 (1993).
Gomez et al., Neuron, vol. 30(1) (2001).
Braunewell et al., Dermentia & Geriatic Cognitive Disorders, vol. 12(2), pp. 110-116 (2001).
Braunwell & Gundelfinger, Cell & Tissue Research, vol. 295(1), pp. 1-12 (1999).
Weiss et al, Journal of Biological Chemistry, vol. 275(51), pp. 40082-40087 (2000).
Rajaram et al, Genesis, vol. 26(4), pp. 234-239 (2000).
De Castro et al, Biochem. & Biophys. Res. Comms., vol. 216(1), pp. 133-140 (1995).
Olafsson et al, Molecular Brain Research, vol. 44(1), pp. 73-82 (1997).
Rivosecchi et al, Journal of Physiology, vol. 474(2), pp. 223-232 (1994).
Grant, Seth G.N., Silva, A.J., Tins, vol. 17(2), pp. 71-75 (1994).

A.

B.

A.

B.

C.

D.

A.

B.

C.

A. Acquisition

B. Extinction

IT Behavior
after conditioning

Expression of the *thy1::cNCS-1* transgene in
lines Tg 26 and Tg 200

A

B

C

D

E

F

Improved associative memory (active avoidance) with the NCS-1 overexpressing line Tg26

A

B the mammalian protein, and frequenin to the *drosophila* protein.

SEQUENCE LISTING

<160> NUMBER OF SEQ ID NOS: 4

<210> SEQ ID NO 1
<211> LENGTH: 3125

<212> TYPE: DNA
<213> ORGANISM: Caenorhabditis elegans

<400> SEQUENCE: 1

| | | | | | |
|---|---|---|---|---|---|
| agctttactg | tttttgaact | aatcatcaat | tagctccacc | tacttttaac | tagatctgtt | 60 |
| aacaacccat | gtagtgatag | cttccctcat | tttcaaacca | atcagcagtt | aggtcaatct | 120 |
| atttctaaac | caatgagcaa | ctgactccgc | ctgttgtgaa | ccaatcaaca | aattagctct | 180 |
| gcctttttg | aaaaaatcaa | taatttgcct | tgaccagcag | aggaaagaaa | agcgacgtta | 240 |
| atagctgatt | aatcttgcta | cacggaacac | ggaacaaatt | tcaagaaagt | atattctatc | 300 |
| aataaaaaaa | ctattacttt | gtaccgagta | ttgtgaaaaa | tcatgaattt | ctgtaaatgt | 360 |
| ttaatttgta | gaaacatgat | ctgtcgccga | aatctgcgcg | aaagttgtgt | ggatcattat | 420 |
| ttcgttaagt | ggaaacatga | tctatttgct | ctttttgat | gaaagaaaca | ttcccaatta | 480 |
| tctgggtttt | cctgaaaact | tttcagtcta | tgttactgct | gttttaattt | aatcttttac | 540 |
| tggaagtcac | gtttaaaatt | ggtttaaaga | ttttattcaa | ttttataaga | tttaaaaaaa | 600 |
| ttgtaggttg | aaaattttca | gtcagagctt | cgaaaagttt | gggataccgt | atatcctcta | 660 |
| ttagtaaggc | gccgttatta | gttttgcacc | tccattagtt | ttgcatcaaa | ttaggtgtcc | 720 |
| gaaaattagt | tttgcatacc | ttactaatag | aggaaatacg | ttttcgtttg | ctccaatttt | 780 |
| ttgttttttt | tttataagga | cagagtaatt | tctattttt | ttcgtattcc | aataattaaa | 840 |
| atataatcag | aaaaataaaa | tcgtaaaaaa | taatatgtta | cgtagacact | cacaatcagg | 900 |
| taggcacaac | gcatttgggt | aatcttctgg | gcaaagtttg | atgcattttt | cccaacccag | 960 |
| ataaagtaa | aaaaaacat | ctaaaaaagt | atcaatcccc | aaaaaaattt | tgatcatttt | 1020 |
| ccagagcttt | gctctcttta | aaactgcttt | ttgatttctt | attcacgtga | aacaattgat | 1080 |
| gttgctccga | tgcacaatgt | gaacttttga | gggttttctg | agccattagc | cactgaccca | 1140 |
| aaatgtgcag | tctggaagat | attaattttt | tgcttttttt | ctagaagttt | tcttgcagtg | 1200 |
| tttgaaagtt | ttaagacctc | tcatttgcca | tcttactatt | agtggaattt | cttcaaggaa | 1260 |
| tttctcaatt | tcaaattcct | actgactggc | tgttttcaaa | aaattacaca | tcatagtttt | 1320 |
| aatgaaaaat | cataggttta | atcatagttg | taatggaaaa | aaccaggtat | attacacaag | 1380 |
| cacccaaaaa | aattccagca | gtggcttggt | tatggcgatt | tccggcaatc | ggtcattgac | 1440 |
| cgttttcaga | aaataggttt | gtcacctaaa | aattctaatc | aggtaataat | aatagatttc | 1500 |
| gtgatagggg | ataattctta | atagtaaact | ttaaaatatt | ttttctctt | tcaatgatat | 1560 |
| gacagattca | tcttgatttc | cggttttgtt | taagatctga | ataattccaa | aaacattcat | 1620 |
| agctttgata | ttggttagtt | gtgacttagc | acccaaaaat | aatttactttt | agcagtttta | 1680 |
| attcaaaata | aaataattct | gcgtaaaatt | tctaaatttt | tcaactttttt | atcaagatttt | 1740 |
| tgtcgagtaa | tgctacttca | tcaaaacttc | ttactccatc | ggttgctccg | acttcttcc | 1800 |
| aatccaaaac | atgtaaactc | aactatcttt | tctctatttt | tagagtcctc | caaaaccata | 1860 |
| tgtctgtttg | cgcgtgcgtg | agatattttc | ccccttatg | cacactcatt | ttgtggttat | 1920 |
| tcataaaaat | gaaatataca | tctagagaga | aaagttagag | agtcgtagag | aaaatagaaa | 1980 |
| ttgtattgca | ccatgatttt | gtcttctttt | tttgccttcc | ccttggagca | aaatcgctaa | 2040 |
| tcctagctac | gccagtgatt | gggttgctat | ggatctcgtg | cacacttgct | tcatgtaca | 2100 |
| tatgtatttt | ctcacatatt | cggttttccc | cttttttga | tatctatata | ctgccggccg | 2160 |
| ccgtgcacct | catttttctc | tcctcgctcc | gcacaccatt | tctgtgtgcc | tctgacggat | 2220 |

```
aaactgatgg gcatccggag cttactggtg acgtttgagg cggctcttct cccctatagg   2280
aagtttggaa ttatggcctt gagtgactgg aaaaagaag agataactcg cataaacttc    2340
atatttcccc ttcattttgc tcatcaaatt tttgcccta ttttaccaga gatttgcaga    2400
agaactagtt agttacgatg atggaacaaa atagtcaagt cctagcgcac tgaccaagac   2460
taccgttttg cactgaccaa ttttttagatc tgaccaaaaa tttttaagc aatagcaaaa   2520 atgttttgtt tgcactgacc aacatttta gcactttatt ctgcaccgac caatattctt    2580
tcagatatca actattttcc tattgcacca aagcatatca aaatttgata cagctttcaa   2640
aatatataat gttatttatt tgttcttaag ttgccgagta tattaataca actgctattt   2700
taaaatactt tgccagttta cggttgcttg aacacccaag aaactgaaaa aaaaattcaa   2760
ttccaggtaa aaatgtattc cactcaagcc tcctatcctc caaaacctaa gtaaattttc   2820
gaagatttag ttttcttttt ttcctggagt ttagttgatt gtgctcccta cactttgttt   2880
tctttatatt cttaccactt ctctacccct ttataccatt gagaacccgc cgaaacacat   2940 cgttttatt caattaatgt cattttattg gttctcacac ccccaatct gctttcacta    3000 tattattttt tttgtctagt ttccgtattt gaacgttgct actatttta ttttcagata   3060 acaaaaaga gagaatcaag ttgcaaatca aaattatttt attagaattg ttgcgaagaa   3120
ggatc                                                              3125

<210> SEQ ID NO 2
<211> LENGTH: 215
<212> TYPE: DNA
<213> ORGANISM: Gallus gallus

<400> SEQUENCE: 2
tcccagggcc gagcggcgct tacggggaag acgctctctg tgccatccga ccacgcagcg   60
atgcttgcct gccctctcc agccctcctc catgccccac gagccaagat gcagcacagt   120
gccactcacg cccctctgcg ctccgaacca tcgccggtgc catctgccaa cttctgcttt   180
ttttccaaca aaaacaaaa atcacccaaa aaaa                               215

<210> SEQ ID NO 3
<211> LENGTH: 18
<212> TYPE: DNA
<213> ORGANISM: Gallus gallus

<400> SEQUENCE: 3
ccacagaatc caagtcgg                                                18

<210> SEQ ID NO 4
<211> LENGTH: 19
<212> TYPE: DNA
<213> ORGANISM: Mus musculus

<400> SEQUENCE: 4
atacgagccc gtcgtagag                                               19
```

METHOD FOR IDENTIFYING AN AGONIST OF NEURONAL CALCIUM SENSOR-1 (NCS-1), FOR THERAPY OF CNS DISORDERS

BACKGROUND OF THE INVENTION

The neuronal calcium sensor-1 (NCS-1) is an intracellular calcium sensor of the EF-hand calcium-binding proteins family that is neuron-specific and highly conserved throughout evolution with 100% identity at the amino acid level among vertebrates, and 75% between vertebrates and *C. elegans* (Braunewell and Gundelfinger, 1999; De Castro et al., 1995). NCS-1 binds 3 calcium ions with a high affinity of ~300 nM that is within the range of intracellular $Ca^{2+}_i$ fluctuations known to regulate key neuronal functions such as neurotransmitter release, receptor phosphorylation, ion channel activities, or transcription (Bourne et al., 2001; Burgoyne and Weiss, 2001; Cox et al., 1994; Fontana and Blaustein, 1993; Martone et al., 1999; Paterlini et al., 2000; Yazejian et al., 2000). In a calcium-dependent manner, the recombinant vertebrate NCS-1 can activate, in vitro, the G-protein receptor kinase 1 (De Castro et al., 1995; Iacovelli et al., 1999), substitute for calmodulin (CaM) and directly activate CaM-dependent targets such as 3':5'-cyclic nucleotide phosphodiesterase, calcineurin, and nitric oxide synthase enzymes (Schaad et al., 1996). NCS-1 has also been reported to regulate evoked exocytosis in neuroendocrine cells (McFerran et al., 1998). Phenotypic analyses addressing the functional role of NCS-1 in vivo have been performed with yeast, *Paramecium, C. elegans*, and *Drosophila*. In *S. cerevisiae*, the frq1 gene encodes NCS-1 which is essential for vegetative growth, and which has been shown, following genetic studies, to interact with the yeast phosphatidylinositol 4-OH kinase Pik1 (Hendricks et al., 1999). The vertebrate NCS-1 directly substitutes for a mutated form of CaM in *Paramecium* and can restore normal wild-type (WT) behavioral responses (avoiding reaction) of live *Paramecium* mutants most likely via the re-activation of a CaM-dependent potassium channel (Schaad et al., 1996). A shaker-like phenotype in *Drosophila* caused by the overexpression of frequenin (Pongs et al., 1993), the *Drosophila* orthologue of NCS-1, seems to involve an increase of evoked neurotransmitter release at the neuromuscular junction (NMJ) of flies via unknown mechanisms that could possibly involve the NCS-1-dependent regulation of a $K^+$ channel (Poulain et al., 1994) or of a $Na^+$-$Ca^{2+}$ exchanger (Rivosecchi et al., 1994). However, the function of NCS-1, if any, in terms of particular phenotypic characteristics responsive to NCS-1 activity remained unknown.

SUMMARY OF THE INVENTION

The present invention provides a method for determining whether an agent is an agonist of the neuron-specific calcium sensor-1 (NCS-1), for consideration of an agonist of NCS-1 as a drug candidate for therapy of a behavioral disorder or for improving learning and/or memory of a subject, said method comprising the steps of:
  (a) contacting a cell, tissue or non-human animal with an agent to be screened under conditions to permit neuron-specific calcium sensor-1 (NCS-1) activity; and
  (b) determining NCS-1 activity of said treated cell, tissue or non-human animal, wherein an increase in NCS-1 activity compared with a corresponding control cell, tissue or animal is indicative of an agent which is an agonist of NCS-1.

The present invention also provides a method for determining whether a patient has a CNS disorder or is at risk for developing a CNS disorder. In one embodiment, the method comprises determining the presence or absence of a mutation in the polynucleotide encoding neuron-specific calcium sensor-1 (NCS-1) in a biological sample from the patient, wherein the presence of said mutation indicates that the patient has a CNS disorder or is at risk for developing a CNS disorder.

In another embodiment, the method for determining whether a patient has a CNS disorder or is at risk for developing a CNS disorder comprises:
  (a) determining the concentration of a neuron-specific calcium sensor-1 (NCS-1) polypeptide in a biological sample from a patient; and
  (b) determining whether NCS-1 in the sample is present in a concentration lower than that in a control sample, wherein a lower concentration of NCS-1 as compared to control indicates the patient has a CNS disorder or is at risk for developing a CNS disorder.

Furthermore, a transgenic non-human animal or a transgenic cell or tissue thereof is provided, wherein the transgenic non-human animal displays a substantially reduced level of NCS-1 activity compared to the corresponding wild type animal, and comprises at least one mutant allele of the NCS-1 encoding gene.

DETAILED DESCRIPTION OF THE INVENTION

The present invention implicates CNS function via the neuronal calcium sensor NCS-1, which can be used as a novel target for therapeutic intervention.

Accordingly, in one aspect the present invention relates to a pharmaceutical composition comprising an agonist/activator or antagonist/inhibitor of neuron-specific calcium sensor-1 (NCS-1), and a pharmaceutically acceptable carrier.

In accordance with the present invention, the neuronal role of ncs genes in vivo has been characterized by loss-of-function genetics in a eukaryotic organism. To investigate the role of NCS-1 as a regulator of neuronal activity in vivo, *C. elegans* has been chosen as a model organism due to its simple nervous system and well-described neuronal circuitry with the ability to respond to diverse environmental stimuli such as touch, smell, taste or temperature. Furthermore, a vertebrate model of associative learning and memory with two transgenic mouse lines has been used.

The nucleotide and amino acid sequences of NCS-1 are known. Furthermore, the coding sequences of NCS-1 genes can be retrieved from public data bases, such as from NCBI; see for example accession numbers XM-005625 and NM-014286 describing NCS-1 as the *Homo sapiens* frequenin (*Drosophila*) homolog (FREQ), NM-019681 describing the *Mus musculus* NCS-1 or frequenin homolog, AL447416 describing a *Paramecium* homolog of NCS-1, AF020184 describing mouse neuronal calcium sensor-1 (NCS-1) mRNA, L27421 describing rat neuronal calcium sensor (NCS-1), L33680 describing *Caenorhabditis elegans* neuronal calcium binding protein (NCS-1), and L27420 describing an avian (Gallus gallus) neuronal calcium sensor (NCS-1) and references cited in the annotations. Although NCS-1 and frequenin are the same, NCS-1 will refer herein to the mammalian protein, and frequenin to the *drosophila* protein.

A functional role of NCS-1 for the phenotype of a living organism has been recognized in connection with the present invention using the model system *C. elegans*. On a radial temperature gradient *C. elegans* worms migrate, after conditioning with food, toward their cultivation temperature and move along this isotherm. This experience-dependent behavior is called isothermal tracking (IT). Experiments performed in accordance with the present invention surprisingly show that the neuron-specific calcium sensor-1 (NCS-1), a protein highly conserved through evolution, is essential for optimal IT behavior. ncs-1 knockout animals show major defects in IT behavior, although their chemotactic, locomotor and thermal avoidance behaviors are normal. The knockout phenotype can be rescued by re-introducing wild-type NCS-1 into the AIY interneuron, a key component of the thermotaxis network. A loss of function form of NCS-1 incapable of binding calcium does not restore IT behavior, whereas NCS-1 overexpression enhances IT behavior performance levels, accelerates learning (faster acquisition), and produces a memory with slower extinction. Thus, proper calcium signaling via the neuronal calcium sensor NCS-1 defines a novel pathway essential for associative learning and memory. In a further set of experiments, a vertebrate model of associative learning and memory with two transgenic mouse lines has been studied, Tg26 and Tg200, overexpressing different amounts of NCS-1 into distinct brain regions. When compared to WT controls, both lines show a significant increase in hippocampal CA1 long-term potentiation (LTP), which is well correlated with the amount of NCS-1. Overexpression of NCS-1 in motor neurons results in higher and faster synaptic fatigue, an observation compatible with a presynaptic enhancement of neurotransmitter release by NCS-1. At the behavioral level, overexpression of NCS-1 in Tg26 produces better learning and memory performances in the Morris water maze and active avoidance tasks. Together, these data indicate that calcium signaling via NCS-1 (a protein identical among vertebrates) regulates a pathway essential for learning and memory processes in both invertebrates and vertebrates. These findings also implicate that NCS-1 or compounds capable of modulating the activity of NCS-1 can be used for the treatment of disorders of the CNS, in particular those that display phenotypes related to altered behavior and loss of memory. Accordingly, the present invention provides the use of NCS-1 and compounds capable of modulating the activity or the amount of active NCS-1 for amelioration of CNS disorders which are related to the malfunction of the NCS-1 gene or its gene product. Furthermore, such compounds can be used for the treatment of symptoms of CNS disorders which are caused by mutant genes other than NCS-1 and/or are caused by the exposure to certain environmental conditions, for example stress, pollution, heat, poisoning, drug abuse, smoking, and the like. In addition, disorders resulting from aging processes such as loss of memory may be effectively treated with compounds capable of modulating NCS-1 activity or by elevating the amount of active NCS-1 protein. The method of the present invention will help to identify and obtain such compounds which are drug candidates for the treatment of the mentioned disorders. Prominent examples of such disorders are Schizophrenia, Alzheimer's Disease, Parkinson's Disease, Major Depression, Bipolar Disorder, Anxiety Disorders, Appetite Disorders, Sleep Disorders, Insomnia, Attention Deficit Hyperactivity Disorder, drug abuse, and other.

Accordingly, the present invention relates to the use of an agonist/activator or of an antagonist/inhibitor of neuron-specific calcium sensor-1 (NCS-1) or a pharmaceutically acceptable salt thereof for the preparation of a composition for the treatment of a CNS disorder or for improving cognition of a subject. Preferably, said CNS disorder is Schizophrenia, Alzheimer's Disease, Parkinson's Disease or hyperactivity.

The terms "antagonist/inhibitor and agonist/activator" in accordance with the present invention include chemical agents that modulate the action of NCS-1, either through altering its enzymatic activity or through modulation of expression, e.g., by affecting transcription or translation. In some cases the antagonist/inhibitor or agonist/activator may also be a substrate or ligand binding molecule.

The term "activator," as used herein, includes both agonists necessary for the NCS-1 to become active in the first place, and agonists which accentuate its activity. The term "inhibitor" includes both substances which reduce the activity of the NCS-1 and these which eliminate it. When more than one possible activity is defined for NCS-1, for example calcium binding, increase of long-term potentiation in the hippocampus, facilitation of transmitter release and/or any other activity described in the background section above, the inhibitor or activator may modulate any or all of NCS-1 activities. An "antagonist" or "agonist" that modulates the activity of NCS-1 and causes for example a response in a cell based assay described below, refers to a an agent, e.g., a compound, that alters directly or indirectly the activity of NCS-1 or the amount of active NCS-1. Typically, the effect of an antagonist is observed as a blocking of agonist-induced activation of calcium signalling. Antagonists include competitive as well as non-competitive antagonists. A competitive antagonist (or competitive blocker) interacts with or near the site specific for agonist binding. A non-competitive antagonist or blocker inactivates the function of NCS-1 by interacting with a site other than the agonist interaction site. Preferably, the antagonist/inhibitor and agonist/activator of NCS-1 are small chemical agents which directly interact with NCS-1. Therefore, there will preferably be a direct relationship between the molar amount of compound required to inhibit or stimulate NCS-1 activity and the molar amount of NCS-1 present or lacking in the cell.

Activators and inhibitors may be designed by structure-assisted computer modeling, for example according to alpha-helix and alpha-helix forming regions ("alpha-regions"), beta-sheet and beta-sheet-forming regions ("beta-regions"), turn and turn-forming regions ("tum-regions"), coil and coil-forming regions ("coil-regions"), hydrophilic regions, hydrophobic regions, alpha amphipathic regions, beta amphipathic regions, flexible regions, surface-forming regions, substrate binding region, and high antigenic index regions. Such preferred regions include Garnier-Robson alpha-regions, beta-regions, turn-regions, and coil-regions, Chou-Fasman alpha-regions, beta-regions, and turn-regions, Kyte-Doolittle hydrophilic regions and hydrophobic regions, Eisenberg alpha and beta amphipathic regions, Karplus-Schulz flexible regions, Emini surface-forming regions, and Jameson-Wolf high antigenic index regions. Computer predictions can be made using for example GCG-software derived from HGMP resource center Cambridge (Rice, 1995) Programme Manual for the EGCG package. (Cambridge, CB10 1RQ, England: Hinxton Hall).

In one embodiment of the pharmaceutical composition and the use of the present invention, the agonist/activator is or is derived from an NCS-1 polypeptide, an anti-NCS-1 antibody, a transcription regulator of the ncs-1 gene, a ligand binding molecule, a calcium mimetic or a derivative of a calmodulin activator.

Using known methods of protein engineering and recombinant DNA technology, variants may be generated to improve or alter the characteristics of the NCS-1 polypeptides. For instance, one or more amino acids can be deleted from the N-terminus or C-terminus of the protein without substantial loss of biological function. The authors of Ron, J. Biol. Chem. 268 (1993), 2984-2988, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeii, J. Biotechnology 7 (1988), 199-216).

Moreover, ample evidence demonstrates that variants often retain a biological activity similar to that of the naturally occurring protein. For example, Gayle and coworkers (J. Biol. Chem. 268 (1993); 22105-22111) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]"; see Abstract. In fact, only 23 unique amino acid sequences, out of more than 3,500 nucleotide sequences examined, produced a protein that significantly differed in activity from wild-type. Furthermore, using the PESTFIND program (Rogers, Science 234 (1986), 364-368), PEST sequences (rich in proline, glutamic acid, serine, and threonine) can be identified, which are characteristically present in unstable proteins. Such sequences may be removed from the NCS-1 proteins in order to increase the stability and optionally the activity of the proteins. Methods for introducing such modifications in the nucleic acid molecules according to the invention are well-known to the person skilled in the art.

Thus, the present invention includes the use of NCS-1 polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, Science 247 (1990), 1306-1310, wherein the authors indicate that there are two main strategies for studying the tolerance of an amino acid sequence to change.

Besides conservative amino acid substitution, variants of NCS-1 include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretary sequence, or a sequence facilitating purification. Such variant polypeptides are deemed to be within the scope of those skilled in the art from the teachings herein.

For example, NCS-1 polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity; see, e.g. Pinckard, Clin. Exp. Immunol. 2 (1967), 331-340; Robbins, Diabetes 36 (1987), 838-845; Cleland, Crit. Rev. Therapeutic Drug Carrier Systems 10 (1993), 307-377.

An anti-NCS-1 antibody to be used in accordance with pharmaceutical compositions of the present invention can be monoclonal antibody, a polyclonal antibody, a single chain antibody, human or humanized antibody, primatized, xenogeneic, chimerized or fragment thereof that specifically binds an NCS-1 peptide or polypeptide and also including bispecific antibody, synthetic antibody, antibody fragment, such as Fab, Fv or scFv fragments etc., or a chemically modified derivative of any of these. The general methodology for producing antibodies is well-known and has been described in, for example, Köhler and Milstein, Nature 256 (1975), 494 and reviewed in J. G. R. Hurrel, ed., "Monoclonal Hybridoma Antibodies: Techniques and Applications", CRC Press Inc., Boco Raron, Fla. (1982), as well as that taught by L. T. Mimms et al., Virology 176 (1990), 604-619. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988.

Further sources for the basic structure of activators or inhibitors can be employed and comprise, for example, mimetic analogs of the NCS-1 polypeptide. Mimetic analogs of the NCS-1 polypeptide or biologically active fragments thereof can be generated by, for example, substituting the amino acids that are expected to be essential for the biological activity with, e.g., stereoisomers, i.e. D-amino acids; see e.g., Tsukida, J. Med. Chem. 40 (1997), 3534-3541. Furthermore, in case fragments are used for the design of biologically active analogs pro-mimetic components can be incorporated into a peptide to reestablish at least some of the conformational properties that may have been lost upon removal of part of the original polypeptide; see, e.g., Nachman, Regul. Pept. 57 (1995), 359-370. Furthermore, the NCS-1 polypeptide can be used to identify synthetic chemical peptide mimetics that bind to or can function as a ligand, substrate, binding partner or the receptor of the NCS-1 polypeptide as effectively as does the natural polypeptide; see, e.g., Engleman, J. Clin. Invest. 99 (1997), 2284-2292. For example, folding simulations and computer redesign of structural motifs of the protein of the invention can be performed using appropriate computer programs (Olszewski, Proteins 25 (1996), 286-299; Hoffman, Comput. Appl. Biosci. 11 (1995), 675-679). Computer modeling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). In particular, the appropriate programs can be used for the identification of interactive sites of the NCS-1 polypeptide and its ligand or other interacting proteins by computer assistant searches for complementary peptide sequences (Fassina, Immunomethods 5 (1994), 114-120. Further appropriate computer systems for the design of protein and peptides are described in the prior art, for example in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, a three-dimensional and/or crystallographic structure of the NCS-1 protein can be used for the design of mimetic inhibitors of the biological activity of the protein of the invention (Rose, Biochemistry 35 (1996), 12933-12944; Rutenber, Bioorg. Med. Chem. 4 (1996), 1545-1558).

The structure-based design and synthesis of low-molecular-weight synthetic molecules that mimic the activity of the native biological polypeptide is further described in, e.g., Dowd, Nature Biotechnol. 16 (1998), 190-195; Kieber-Emmons, Current Opinion Biotechnol. 8 (1997), 435-441; Moore, Proc. West Pharmacol. Soc. 40 (1997), 115-119; Mathews, Proc. West Pharmacol. Soc. 40 (1997), 121-125; Mukhija, European J. Biochem. 254 (1998), 433-438.

It is also well known to the person skilled in the art that it is possible to design, synthesize and evaluate mimetics of small organic compounds that, for example, can act as a substrate or ligand to the NCS-1 polypeptide. For example, it has been described that D-glucose mimetics of hapalosin exhibited similar efficiency as hapalosin in antagonizing multidrug resistance assistance-associated protein in cytotoxicity; see Dinh, J. Med. Chem. 41 (1998), 981-987.

The polynucleotides encoding NCS-1 can also serve as a target for activators and inhibitors. Activators may comprise, for example, proteins that bind to the mRNA of a gene encoding a NCS-1 polypeptide, thereby stabilizing the native conformation of the mRNA and facilitating transcription and/or translation, e.g., in like manner as Tat protein acts on HIV-RNA. Furthermore, methods are described in the literature for identifying nucleic acid molecules such as an RNA fragment that mimics the structure of a defined or undefined target RNA molecule to which a compound binds inside of a cell resulting in retardation of cell growth or cell death; see, e.g., WO 98/18947 and references cited therein. These nucleic acid molecules can be used for identifying unknown compounds of pharmaceutical and/or agricultural interest, and for identifying unknown RNA targets for use in treating a disease. Alternatively, for example, the conformational structure of the RNA fragment which mimics the binding site can be employed in rational drug design to modify known ligands to make them bind more avidly to the target. One such methodology is nuclear magnetic resonance (NMR), which is useful to identify drug and RNA conformational structures. Still other methods are, for example, the drug design methods as described in WO 95/35367, U.S. Pat. No. 5,322,933, where the crystal structure of the RNA fragment can be deduced and computer programs are utilized to design novel binding compounds which can act as antibiotics.

Some genetic changes lead to altered protein conformational states. For example, some mutant NCS-1 proteins may possess a tertiary structure that renders them far less capable of facilitating calcium signaling. Restoring the normal or regulated conformation of mutated proteins is the most elegant and specific means to correct these molecular defects, although it may be difficult. Of particular interest in this regard are the following domains of NCS-1: The 3 functional calcium binding sites called EF-hands (EF) at amino acid positions 73-84 (EF2), 109-120 (EF3), 157-168 (EF4) and the surrounding amino acid sequences or positions interacting with the calcium binding site. In addition, the former calcium binding site (EF1), at position 36-47 might contribute to calcium binding or regulate NCS-1 function. Finally, the N-terminus (i.e. amino acids 1-8) may serve as a myristoylation site and could provide a regulatory function of NCS-1. Pharmacological manipulations thus may aim at restoration of wild-type conformation of the NCS-1 protein. Thus, the present invention also uses molecules which are capable of activating the wild-type, i.e. "NCS-1" or "anti-NCS-1" function of a NCS-1 protein.

Recombinant NCS-1 polynucleotides, antisense molecules, vectors incorporating such polynucleotides or antisense molecules can be produced by methods known to those skilled in molecular biology. For example, the choice of vectors would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989), (1994). Alternatively, the polynucleotides and vectors can be reconstituted into liposomes for delivery to target cells. Relevant sequences can be transferred into expression vectors where expression of a particular polypeptide is required. Typical cloning vectors include pBscpt sk, pGEM, pUC9, pBR322 and pGBT9. Typical expression vectors include pTRE, pCAL-n-EK, pESP-1, pOP13CAT, pET, pGEX, pMALC, pPIC9, pBac.

In another embodiment of the pharmaceutical composition and the use of the present invention, the antagonist/inhibitor is or is derived from an NCS-1 polypeptide, an anti-NCS-1 antibody, an ncs-1 antisense nucleic acid molecule, a ligand binding molecule, a calcium chelator or a calmodulin inhibitor. Preferably, said antagonist/inhibitor interfere with calcium binding of NCS-1 or change the conformation/function of NCS-1.

The antibodies, nucleic acid molecules, inhibitors and activators used in the compositions of the present invention preferably have a specificity at least substantially identical to the binding specificity of the natural ligand or binding partner of the NCS-1 protein, in particular if NCS-1 stimulation is desired. An antibody or inhibitor can have a binding affinity to the NCS-1 protein of at least $10^5$ $M^{-1}$, preferably higher than $10^7$ $M^{-1}$ and advantageously up to $10^{10}$ $M^{-1}$ in case NCS-1 suppression should be mediated.

In a preferred embodiment, a suppressive antibody or inhibitor has an affinity of at least about $10^{-7}$ M, preferably at least about $10^{-9}$ M and most preferably at least about $10^{-11}$ M; and a NCS-1 stimulating activator has an affinity of less than about $10^{-7}$ M, preferably less than about $10^{-6}$ M and most preferably in order of $10^{-5}$M.

In case of antisense nucleic acid molecules it is preferred that they have a binding affinity to those encoding the NCS-1 protein of at most 2-, 5- or 10-fold less than an exact complement of 20 consecutive nucleotides of the coding sequence.

Preferably, the agonist/activator and antagonist/inhibitor is not larger than the "bioavailability wall" of 500-600 Da in order to be able to cross the lipophilic cell membrane into the cell. On the other hand, in protein therapy it has been recently demonstrated that enzymes fused to part of a protein from the HIV virus can cross cell membranes while retaining their enzymatic activity in vivo in mice (Schwarze, Science 285 (1999), 1569-1572). It has been known for approximately ten years that the transactivating regulatory protein (TAT protein) from the HIV virus has an unusual ability to cross cell membranes without using receptors or transporters, or requiring ATP (Green and Loewenstein, Cell 55 (1988), 1179-1188). Although its exact mechanism is unknown, it has been shown that the protein transduction domain (PTD) of TAT opens a "hole" in the cell membrane lipid bilayer, pulling anything covalently attached through it, before closing it again. This is a specific process that does not otherwise damage the cell. Thus, a functional NCS-1 protein, anti-NCS-1 antibody or other compounds may be coupled to PTD via a linker in order to let them cross the cell membrane; see also for review DDT 4 (1999), 537.

In a further aspect, the present invention relates to a cell based method of identifying and obtaining a drug candidate for therapy of a CNS disorder or for improving cognition of a subject, said method comprising the steps of (a) screening a cell, tissue or non-human animal with a compound to be screened under conditions to permit neuron-specific calcium sensor-1 (NCS-1) activity; and (b) determining NCS-1 activity of said treated cell, tissue or non-human animal, wherein a difference in NCS-1 activity compared with a corresponding control cell, tissue or animal is indicative for a drug candidate; and optionally (c) obtaining the drug candidate determined to alter NCS-1 activity in step (b).

The amount of time necessary for cellular contact with the compound is empirically determined, for example, by running a time course with a known NCS-1 modulator and measuring cellular changes as a function of time. The measurement means of the method of the present invention can be further defined by comparing a cell that has been exposed to a compound to an identical cell that has not been similarly exposed to the compound. Alternatively two cells, one containing functional NCS-1 and a second cell identical to the first, but lacking functional NCS-1 could both be contacted with the same compound and compared for differences between the two cells. This technique is also useful in establishing the background noise of these assays. One of average skill in the art will appreciate that these control mechanisms also allow easy selection of cellular changes that are responsive to modulation of functional NCS-1.

The term "cell" refers to at least one cell, but includes a plurality of cells appropriate for the sensitivity of the detection method. Cells suitable for the present invention may be bacterial, yeast, or preferably eukaryotic. The methods of this invention employ certain types of cells, certain observations of changes in aspects of the biological state of a cell, and certain comparisons of these observed changes. In the following, these cell types, observations, and comparisons are described in turn in detail.

The present invention makes use of three principal types of cells: wild-type cells, modified cells i.e. transgenic cells, compound- or drug-exposed cells. "Wild-type" cells are reference, or standard, cells used in a particular application or embodiment of the methods of this invention. Being only a reference cell, a wild-type cell, need not be a cell normally found in nature, and often will be a recombinant or genetically altered cell line. Usually the cells are cultured in vitro as a cell line or strain. Other cell types used in the particular application of the present invention are preferably derived from the wild-type cells. Less preferably, other cell types are derived from cells substantially isogeneic with wild-type cells. For example, wild-type cells might be a particular cell line of the yeast Saccharomyces cerevisiae, or a particular mammalian cell line (e.g., HeLa cells). Although, for simplicity this disclosure often makes reference to single cells (e.g., "screening a cell"), it will be understood by those of skill in the art that more often any particular step of the invention will be carried out using a plurality of genetically identical cells, e.g., from a cultured cell line. Two cells are said to be "substantially isogeneic" where their expressed genomes differ by a known amount that is preferably at less than 10% of genetic loci, more preferably at less that 1%, or even more preferably at less than 0.1%. Alternately, two cells can be considered substantially isogeneic when the portions of their genomes relevant to the effects of a drug of interest differ by the preceding amounts. It is further preferable that the differing loci be individually known. "Compound- or drug-exposed" cells are, briefly, either wild-type cells or modified cells that have been exposed to (a) compound(s) of interest, e.g., drug candidate(s).

"Modified cells" are derived from wild-type cells by modifications to a particular cellular constituent. Methods of modification are adaptable to this invention if they alter, either by increasing or decreasing, preferably only a single targeted cellular constituent, or less preferably at most only a few targeted cellular constituents (e.g., from 2 to 5 cellular constituents), that influence the aspect of the biological state of a cell measured in an embodiment of this invention. Preferable modification methods are capable of individually targeting and altering many measured cellular constituents relevant to an aspect of the biological state, and most preferably are capable of targeting and altering a substantial fraction of such cellular constituents. For example, preferable modification methods are capable of targeting and altering, e.g., a substantial fraction of all the genes, proteins, or protein activities in a cell, or at least a substantial fraction of those constituents relevant to characterizing the effects of a drug of interest. Normally, the modified will be a transgenic cell.

The above-described cells can also be comprised in a tissue or organism, i.e. non-human animal. General methods for the screening of compounds that have a desired effect on a cell or organism as measured in a specific assay are described in the prior art; see for example U.S. Pat. No. 6,165,709 and references cited herein.

Cells, non-human animals and NCS-1 expression and/or knock out systems can be found in the art and can be adapted for the method of the present invention; see for example the documents cited in the background section.

The assay methods to determine compound modulation of functional NCS-1 can be in conventional laboratory format or adapted for high throughput. The term "high throughput" refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include 96-well, 384-well or more-well plates, levitating dropplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

The cellular changes suitable for the method of the present invention comprise directly measuring changes in the function or quantity of NCS-1, or by measuring downstream effects of NCS-1 function, for example by measuring secondary messenger concentrations or changes in transcription or by changes in protein levels of genes that are transcriptionally influenced by NCS-1, or by measuring phenotypic changes in the cell. Preferred measurement means include changes in the quantity of NCS-1 protein, changes in the functional activiy of NCS-1, changes in the quantity of mRNA, changes in intracellular protein, changes in cell surface protein, or secreted protein, or changes in $Ca^{2+}$, cAMP or GTP concentration. Changes in the quantity or functional activity of NCS-1 are described herein. Said functional activity is preferably calcium binding. Changes in the levels of mRNA are detected by reverse transcription polymerase chain reaction (RT-PCR), by differential gene expression or by microarrays. Immunoaffinity, ligand affinity, or enzymatic measurement quantitates changes in levels of protein in host cells. Protein-specific affinity beads or specific antibodies are used to isolate for example $^{35}$S-methionine labelled or unlabelled protein. Labelled protein is analyzed by SDS-PAGE. Unlabelled protein is detected by Western blotting, cell surface detection by fluorescent cell sorting, cell image analysis, ELISA or RIA employing specific antibodies. Where the protein is an enzyme, the induction of protein is monitored by cleavage of a flourogenic or colorimetric substrate.

Where the endogenous gene encodes a soluble intracellular protein, changes in the endogenous gene may be measured by changes of the specific protein contained within the cell lysate. The soluble protein may be measured by the methods described herein.

The present invention is also directed to methods for screening for compounds that modulate the expression of DNA or RNA encoding NCS-1 as well as the function of NCS-1 protein in vivo. Compounds may modulate by increasing or attenuating the expression of DNA or RNA encoding NCS-1, or the function of NCS-1 protein. Compounds that modulate the expression of DNA or RNA encoding NCS-1 or the function of NCS-1 protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents.

The above-described methods can, of course, be combined with one or more steps of any of the above-described screening methods or other screening methods well known in the art. Methods for clinical compound discovery comprise for example ultrahigh-throughput screening (Sundberg, Curr. Opin. Biotechnol. 11 (2000), 47-53) for lead identification, and structure-based drug design (Verlinde and Hol, Structure 2 (1994), 577-587) and combinatorial chemistry (Salemme et al., Structure 15 (1997), 319-324) for lead optimization.

Once a drug has been selected, the method can have the additional step of repeating the method used to perform rational drug design using the modified drug and to assess whether said modified drug displays better affinity according to for example interaction/energy analysis.

In a preferred embodiment of the method of the present invention, said cell, tissue or non-human animal is a transgenic cell, tissue or non-human animal which displays a substantially reduced or enhanced level of neuron-specific calcium sensor-1 (NCS-1) activity compared to a corresponding wild-type cell, tissue or non-human animal.

Preferably said substantially reduced or enhanced level of NCS-1 activity results in an altered and a typic response of the transgenic cell, tissue or non-human animal. An agonist/activator or antagonist/inhibitor will then be identified by observing whether a candidate compound is able at a certain concentration to revert the phenotypic response of said transgenic cell, tissue or non-human animal back to normal. In a particular preferred embodiment, said transgenic non-human animal displays a difference in behavior compared to a wild type non-human animal. In accordance with the present invention, it could be surprisingly shown that in C. elegans NCS-1 activity is linked with isothermal tracking (IT) behavior and also learning mechanisms. Reinforcement via faster acquisition together with higher final performance, not surprisingly, leads to memories that are more persistent, and therefore are consistent with a longer retention period (Milner et al., 1998). However, if extinction is also a learning mechanism, then Tg-ncs-1 worms need more time to react to the absence of one conditioning stimulus (i.e. food) that is likely to be linked to the level of $[Ca^{2+}]_i$ signaling (see FIGS. 5 and 6).

The loss-of-function and mosaic rescue data obtained in accordance with the present invention clearly demonstrate that the presence and amount of the calcium sensor NCS-1 in AIY neurons plays a central role in influencing $Ca^{2+}$-dependent associative learning in C. elegans as demonstrated by its direct regulatory effects on IT behavior. Furthermore, it could be shown that calcium signaling or binding by NCS-1 is critical for this activity, and that the NCS-1 signaling pathway is essential for performing IT behavior. As shown on the schematic diagram (FIG. 6), NCS-1 could have a presynaptic role at the AIY interneuron synapses with AIZ and RIA, or a post-synaptic function at the AFD/AIY synapses. The presynaptic activity of NCS-1 is supported by preliminary data indicating that increased levels of NCS-1 in the mouse hippocampus enhance LTP via a presynaptic facilitation. Similarly, the increase of IT behavior observed when NCS-1 is overexpressed (Tg-ncs-1 animals) may reflect a state where the AIY pre-synaptic terminals are maximally stimulated. The observation of a presynaptic effect on overexpression of NCS-1 at the neuromuscular junction of mice, flies and frogs (Olafsson et al., 1995; Rivosecchi et al., 1994) supports this hypothesis and suggests a conserved function for NCS-1 through evolution.

The AIY interneuron could probably serve as an integrator of food and temperature inputs in the form of $Ca^{2+}$ signals provided by the AFD and surrounding cells. These signals, detected by the neuronal calcium sensor NCS-1, could be transmitted to further downstream targets such as 3':5'-cyclic nucleotide phosphodiesterase, calcineurin, nitric oxide synthase, potassium channels, or phosphatidylinositol 4-OH kinase via mechanisms that could influence AIY synaptic strength. $Ca^{2+}$-signaling via NCS-1 therefore defines a novel pathway for the regulation of synaptic efficacy.

Together, these thermotaxis enhanced or deficient NCS-1 strains provide valuable tools to study synaptic plasticity at the molecular, cellular and network levels using live animals, as well as a model that might well help to understand conserved functions such as long term memory and associative learning across species.

Furthermore, the present examples showed that overexpression of NCS-1 in the mouse resulted in a dose-dependent increase of hippocampal LTP and in enhancement of presynaptic neurotransmitter release at the NMJ. Furthermore, the overexpression of NCS1 in Tg26 line resulted in improved learning performances but was without any effects on emotional responses. It seems that overexpression of NCS-1 in both invertebrate and vertebrate facilitates associative learning and memory processes. This is reflected not only by the very high level of conservation of NCS-1 primary structure through evolution, but also reveals that a common NCS-1-dependent calcium signaling pathway serve as a basic mechanism to regulate synaptic efficacy in different neuronal environments. Indeed, associative learning and memory in C. elegans requires the function of and signaling via NCS-1 in a single inter-neuron receiving a single projection from a sensory neuron and projecting to only two other neuronal cells, whereas in the mouse, NCS-1 seems to regulate the efficacy of the presynaptic terminals (i.e. CA3 neuronal projections on CA1 neurons in the hippocampus, or motorneuron end-plates) that form a very dense and complex network. It is therefore very likely that NCS-1-dependent signaling will be conserved in higher vertebrates, such as monkeys and humans. Provided safe and efficacious gene-delivery systems, it is postulated that overexpression of NCS-1 in the human hippocampus could overcome memory and learning deficits associated with age, or with patients with Alzheimer's, or Schizophrenia diseases.

Usually, said transgenic non-human animal displaying a reduced level of neuron-specific calcium sensor-1 (NCS-1) activity comprises at least one mutant allele of the NCS-1 encoding gene or a corresponding trans-dominant allele of a different gene. Preferably, said transgenic non-human animal is a ncs-1 knock-out animal.

In a particularly preferred embodiment of the method of the present invention, said transgenic non-human animal is *C. elegans* and said behavior is isothermal tracking (IT). As described above and illustrated by the examples, the present invention for the first time provides the functional assay that is able to directly link the molecular action of a modulator of NCS-1 activity with a phenotypic response of a test animal. Since *C. elegans* is well characterized, easy to handle, and culture conditions and other factors can be easily controlled, this test animal is particularly suited for high throughput screening; see for example Link et al., Therapeutic target discovery using *C. elegans*. Pharmacogenomics 1 (2000), 203-218.

In another particularly preferred embodiment of the method of the invention, said transgenic non-human animal is mice and said behavior is learning and memory performances in the Morris water maze and active avoidance tasks; see also section 6.1.6 of Example 6.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 79 (1994), 193-198 and references cited supra). Furthermore, genes encoding a putative regulator of NCS-1 protein and/or which excert their effects up- or downstream the NCS-1 protein may be identified using, for example, insertion mutagenesis using, for example, gene targeting vectors known in the art. Likewise, the methods of the invention include ENU mutagenesis and suppressor screens that could be preformed to find regulator of NCS-1 dysfunction, hyperfunction, targets, or signaling pathways. Said compounds can also be functional derivatives or analogues of known ligands, for example $Ca^{2+}$. Such useful compounds can also be for example transacting factors which bind to the NCS-1 protein or regulatory sequences of the NCS-1 gene.

The compounds isolated by the above methods can also serve as lead compounds for the development of analog compounds. The analogs should have a stabilized electronic configuration and molecular conformation that allows key functional groups to be presented to the NCS-1 protein or its receptor in substantially the same way as the lead compound. In particular, the analog compounds have spatial electronic properties which are comparable to the binding region, but can be smaller molecules than the lead compound, frequently having a molecular weight below about 2 kD and preferably below about 1 kD. Identification of analog compounds can be performed through use of techniques such as self-consistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art; see also supra. Furthermore, peptidomimetics and/or computer aided design of appropriate derivatives and analogues can be used, for example, according to the methods described above. Methods for the lead generation in drug discovery also include using proteins and detection methods such as mass spectrometry (Cheng et al. J. Am. Chem. Soc. 117 (1995), 8859-8860) and some nuclear magnetic resonance (NMR) methods (Fejzo et al., Chem. Biol. 6 (1999), 755-769; Lin et al., J. Org. Chem. 62 (1997), 8930-8931).

The newly identified drug obtained by a method of the present invention, i.e. an antagonist/inhibitor or agonist/activator can be used for the preparation of a pharmaceutical composition for the treatment of a NCS-1 protein mediated or related disorder. In accordance with this, the present invention also relates to a method of producing a drug comprising the steps of any one of the above-described methods; and (a) synthesizing the drug candidate identified in step (b) or obtained in step (c) or an analog or derivative thereof in an amount sufficient to provide said drug in a therapeutically effective amount to a subject; and/or (b) combining the drug candidate identified in step (b) or obtained in step (c) or an analog or derivative thereof with a pharmaceutically acceptable carrier.

Once a drug has been selected in accordance with any one of the above-described methods of the present invention, the drug or a pro-drug thereof can be synthesized in a therapeutically effective amount. As used herein, the term "therapeutically effective amount" means the total amount of the drug or pro-drug that is sufficient to show a meaningful patient benefit, i.e., treatment, healing, prevention or amelioration of a condition related to an NCS-1 protein, or an increase in rate of treatment, healing, prevention or amelioration of such conditions. In addition or alternatively, in particular with respect to pre-clinical testing of the drug the term "therapeutically effective amount" includes the total amount of the drug or pro-drug that is sufficient to elicit a physiological response, preferably upon its binding to its target NCS-1 protein, in an non-human animal test, preferably in a *C. elegans*, or mice assay such as described herein.

Drugs or pro-drugs after their in vivo administration are metabolized in order to be eliminated either by excretion or by metabolism to one or more active or inactive metabolites (Meyer, J. Pharmacokinet. Biopharm. 24 (1996), 449-459). Thus, rather than using the actual compound or drug identified and obtained in accordance with the methods of the present invention a corresponding formulation as a pro-drug can be used which is converted into its active in the patient. Precautionary measures that may be taken for the application of pro-drugs and drugs are described in the literature; see, for review, Ozama, J. Toxicol. Sci. 21 (1996), 323-329.

The invention further relates to a method of producing a pharmaceutical composition comprising a compound as described above comprising the steps of (a) modifying said compound identified by the method of the invention to achieve (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmakinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carbon acids, or (iii) esterification of hydroxyl groups to, e.g. phosphates, pyrophosphates or sulfates or hemi succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetates, or (xiv) N-acetylation to amides, phenylcarbamates, or (xv) synthesis of Mannich bases, imines, or (xvi) transformation of ketones or aldehydes to Schiff's bases, oximes, acetates, ketales, enolesters, oxazolidines, thiozolidines or combinations thereof; and (b) formulating the product of said modification with a pharmaceutically acceptable carrier.

The various steps recited above are generally known in the art. They include or rely on quantitative structure-action relationship (QSAR) analyses-(Kubinyi, J. Med. Chem. 41 (1993), 2553-2564, Kubinyi, Pharm. Unserer Zeit 23 (1994), 281-290) combinatorial biochemistry, classical chemistry and others (see, for example, Holzgrabe and Bechtold, Pharm. Acta Helv. 74 (2000), 149-155).

As mentioned above, the present invention provides convenient assays, preferably in vivo assays for identifying and obtaining drugs capable of modulating NCS-1 activity, thereby being useful as a therapeutic agent for the treatment of diseases related to NCS-1 activity such as CNS disorders including Schizophrenia, Parkinson's Disease, Alzheimer's Disease, and other behavioral disorders. Thus, the present invention provides therapeutic agents which mode of action is different from compounds previously used for the treatment of the mentioned disorders. In accordance with this, the present invention provides also a use for compounds which have been known in the art, properly also known to be able to modulate NCS-1 activity but which hitherto have not been suggested for medical use because of the lack of knowledge of phenotypic responses of an organism evoked by NCS-1 activity or the lack of it.

A further embodiment of the present invention relates to a pharmaceutical composition comprising a drug or drug candidate identified or obtained by the method of the invention or a racemate, enantiomer, diastereomer, tautomer, mixture of diastereomers or pharmaceutically acceptable salt of any one those, wherein said drug or drug candidate is a modulator of NCS-1 activity. Preferably, said drug facilitates or interferes with calcium binding of NCS-1 or changes conformation of NCS-1.

The present invention also relates to transgenic non-human animals displaying a reduced level of neuron-specific calcium sensor-1 (NCS-1) activity, which comprises at least one mutant allele of the NCS-1 encoding gene or a corresponding trans-dominant allele of a different gene. Preferably, said transgenic non-human animal is a ncs-1 knock-out animal. In a particularly preferred embodiment, said transgenic non-human animal is C. elegans and said behavior is isothermal tracking (IT), or said non-human animal is mice and said behavior is learning and memory performances in the Morris water maze and active avoidance tasks; see also section 6.1.6 of Example 6.

A method for the production of a transgenic non-human animal, for example transgenic mouse, comprises introduction of a NCS-1 polynucleotide or targeting vector into a germ cell, an embryonic cell, stem cell or an egg or a cell derived therefrom. The non-human animal can be used in accordance with a screening method of the invention described herein. Production of transgenic embryos and screening of those can be performed, e.g., as described by A. L. Joyner Ed., Gene Targeting, A Practical Approach (1993), Oxford University Press or mice or Example 6. The DNA of the embryonal membranes of embryos can be analyzed using, e.g., Southern blots with an appropriate probe; see supra. The invention also relates to transgenic non-human animals such as transgenic mouse, rats, hamsters, dogs, monkeys, rabbits, pigs, C. elegans and fish such as Torpedo fish comprising a NCS-1 gene. Preferably, said transgenic non-human animal is C. elegans such as a mutant animal described in the examples. Preferably, the transgenic non-human animal comprises at least one inactivated or suppressed wild type allele of the corresponding NCS-1 encoding gene; see supra. This embodiment allows for example the study of the interaction of various mutant forms of NCS-1 polypeptides on the onset of the clinical symtoms a of disease related to disorders in the calcium signaling pathway. All the applications that have been herein before discussed with regard to a transgenic animal also apply to animals carrying two, three or more transgenes for example encoding calmodulin. It might be also desirable to inactivate NCS-1 protein expression or function at a certain stage of development and/or life-time of the transgenic animal. This can be achieved by using, for example, tissue specific, developmental and/or cell regulated and/or inducible promoters which drive the expression of, e.g., an antisense or ribozyme directed against the RNA transcript encoding the NCS-1 encoding RNA; see also supra. A suitable inducible system is for example tetracycline-regulated gene expression as described, e.g., by Gossen and Bujard (Proc. Natl. Acad. Sci. 89 USA (1992), 5547-5551) and Gossen et al. (Trends Biotech. 12 (1994), 58-62). Similar, the expression of the (mutant) NCS-1 protein may be controlled by such regulatory elements.

Furthermore, the invention also relates to a transgenic, preferably eukaryotic cell which contains (preferably stably integrated into its genome) a NCS-1 nucleic acid molecule or part thereof, wherein the transcription and/or expression of the nucleic acid molecule or part thereof leads to reduction of the synthesis of a NCS-1 protein. In a preferred embodiment, the reduction is achieved by an anti-sense, sense, ribozyme, co-suppression and/or dominant mutant effect. "Antisense" and "antisense nucleotides" means DNA or RNA constructs which block the expression of the naturally occurring gene product.

Techniques how to achieve this are well known to the person skilled in the art. These include, for example, the expression of antisense-RNA, ribozymes, of molecules which combine antisense and ribozyme functions and/or of molecules which provide for a co-suppression effect; see also supra. When using the antisense approach for reduction of the amount of NCS-1 proteins in cells, the nucleic acid molecule encoding the antisense-RNA is preferably of homologous origin with respect to the animal species used for transformation. However, it is also possible to use nucleic acid molecules which display a high degree of homology to endogenously occurring nucleic acid molecules encoding a NCS-1 protein. In this case the homology is preferably higher than 80%, particularly higher than 90% and still more preferably higher than 95%. The reduction of the synthesis of NCS-1 protein in the transgenic eukaryotic cells can result in an alteration in, e.g., calcium signaling. In transgenic animals comprising such cells this can lead to various physiological, developmental and/or morphological changes, preferably to a diminution of cognitive functions such as learning, memory, attention, or hyperactivity. Such behavioral assessments can be performed in rodent and non-rodent species.

Thus, the present invention also relates to transgenic non-human animals comprising the above-described transgenic cells. These may show, for example, a deficiency or other alteration in calcium signaling compared to wild type animals due to the stable or transient presence of a foreign DNA resulting in at least one of the following features:

(a) disruption of (an) endogenous gene(s) encoding NCS-1;
(b) expression of at least one antisense RNA and/or ribozyme against a transcript comprising a NCS-1 polynucleotide;
(c) expression of a sense and/or non-translatable mRNA of an NCS-1 polynucleotide;
(d) expression of an anti-NCS-1 antibody;
(e) incorporation of a functional or non-functional copy of a regulatory sequence of the NCS-1 gene; or
(f) incorporation of a recombinant DNA molecule or vector comprising any one of the above-described polynucleotides or nucleic acid molecules.

With the NCS-1 polypeptides, their encoding polynucleotides arid corresponding vectors, it is now possible to study in vivo and in vitro the efficiency of drugs in relation to particular mutations in NCS-1 proteins of a patient and the affected phenotype. Furthermore, mutant forms of NCS-1 polypeptides can be used to determine the pharmacological profile of drugs and for the identification and preparation of further drugs which may be effective for the treatment of disorders related to the calcium signaling, in particular for the amelioration of certain phenotypes caused by the respective mutations, in the NCS-1 encoding gene.

Over the past 20 years, genetic heterogeneity has been increasingly recognized as a significant source of variation in drug response. Many scientific communications (Meyer, Ann. Rev. Pharmacol. Toxicol. 37 (1997), 269-296 and West, J. Clin. Pharmacol. 37 (1997), 635-648) have clearly shown that some drugs work better or may even be highly toxic in some patients than in others and that these variations in patient's responses to drugs can be related to molecular basis. This "pharmacogenomic" concept spots correlations between responses to drugs and genetic profiles of patient's (Marshall, Nature Biotechnology, 15 (1997), 954-957; Marshall, Nature Biotechnology, 15 (1997), 1249-1252).

In this context of population variability with regard to drug therapy, pharmacogenomics has been proposed as a tool useful in the identification and selection of patients which can respond to a particular drug without side effects. This identification/selection can be based upon molecular diagnosis of genetic polymorphisms by genotyping DNA from leukocytes in the blood of patient, for example, and characterization of disease (Bertz, Clin. Pharmacokinet. 32 (1997), 210-256; Engel, J. Chromatogra. B. Biomed. Appl. 678 (1996), 93-103). For the founders of health care, such as health maintenance organizations in the US and government public health services in many European countries, this pharmacogenomics approach can represent a way of both improving health care and reducing overheads because there is a large cost to unnecessary drugs, ineffective drugs and drugs with side effects.

Hence another object of the present invention concerns the pharmacogenomic selection of drugs and prodrugs for patients suffering from CNS disorders such as those described above and which are possible candidates to drug therapy. Thus, the findings of the present invention provide the options of development of new drugs for the pharmacological intervention with the aim of restoring the function of genetically modified NCS-1 proteins. Also a gene therapeutical approach can be envisaged with the aid of the present invention.

In accordance with the above, the present invention also relates to the use of a neuron-specific calcium sensor-1 (NCS-1) or a biologically active fragment thereof, a nucleic acid molecule encoding NCS-1 or nucleic acid molecule of at least 15 nucleotides in length hybridizing to a ncs-1 gene, an anti-NCS-1 antibody, a cell as described above or of an NCS-1 activity assay for a method of obtaining, identifying and/or profiling a drug candidate for therapy of a CNS disorder or for modulating cognition of subject.

Nucleotide sequences that are complementary to the NCS-1 encoding gene sequence can be synthesized for antisense therapy. These antisense molecules may be DNA, stable derivatives of DNA such as phosphorothioates or methylphosphonates, RNA, stable derivatives of RNA such as 2'-O-alkylRNA, or other NCS-1 antisense oligonucleotide mimetics. NCS-1 antisense molecules may be introduced into cells by microinjection, liposome encapsulation or by expression from vectors harboring the antisense sequence. NCS-1 antisense therapy may be particularly useful for the treatment of diseases where it is beneficial to reduce NCS-1 activity.

NCS-1 gene therapy may be used to introduce NCS-1 into the cells of target organisms. The NCS-1 gene can be ligated into viral vectors that mediate transfer of the NCS-1 DNA by infection of recipient host cells. Suitable viral vectors include retrovirus, adenovirus, adeno-associated virus, herpes virus, vaccinia virus, polio virus and the like. Alternatively, NCS-1 DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo NCS-1 gene therapy. NCS-1 gene therapy may be particularly useful for the treatment of diseases where it is beneficial to elevate NCS-1 activity. Protocols for molecular methodology of gene therapy suitable for use with the NCS-1 gene is described in *Gene Therapy Protocols*, edited by Paul D. Robbins, Human press, Totawa N.J., 1996.

Pharmaceutically useful compositions such as described herein-before, comprising NCS-1 DNA, NCS-1 RNA, or NCS-1 protein, or modulators of NCS-1 activity, i.e. activator/agonist or inhibitor/antagonist, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of NCS-1-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the NCS-1 receptor or its activity while minimizing any potential toxicity. In addition, co-administration or sequential administration of other agents may be desirable.

A therapeutically effective dose refers to that amount of protein or its antibodies, agonists, activators, antagonists, or inhibitors which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of NCS-1 can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a NCS-1 modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the NCS-1 modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinylpyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the disorder. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The present invention also relates to a method of treating a patient in need of such treatment for a disorder which is mediated by neuron-specific calcium sensor-1 (NCS-1), comprising administration of a drug or drug candidate identified or obtained in any one of the above-described methods. In addition, the present invention relates to a method for treating a CNS disorder in a subject or improving cognition of a subject, which method comprises administering to the subject an effective amount of a therapeutic agent to increase the level and/or activity of NCS-1, so as to improve or restore calcium signaling in the subject.

In a preferred embodiment of the uses and methods of the present invention said disorder is or is related to Alzheimer's disease, Parkinson's disease, age-associated cognition deficits, major depression, bipolar disorder, anxiety disorders, appetite disorders, sleep disorders, insomnia, attention deficit hyperactivity disorder or memory loss or a learning deficiency.

In a further aspect the present invention relates to a method of diagnosing a pathological condition or a susceptibility to a pathological condition in a subject related to a CNS disorder:

(a) determining the presence or absence of a mutation in the polynucleotide encoding neuron-specific calcium sensor-1 (NCS-1); and (b) diagnosing a pathological condition or a susceptibility to a pathological condition based on the presence or absence of said mutation.

In another embodiment the present invention relates to a method of diagnosing a pathological condition or a susceptibility to a pathological condition in a subject related to a CNS disorder comprising:

(a) determining the presence or amount of expression of a neuron-specific calcium sensor-1 (NCS-1) polypeptide in a biological sample; and (b) diagnosing a pathological condition or a susceptibility to a pathological condition based on the presence or amount of expression of the polypeptide.

In these embodiments, the NCS-1 polynucleotides, nucleic acid molecules, (poly)peptide, antibodies or compounds identified above are preferably detectably labeled. A variety of techniques are available for labeling biomolecules, are well known to the person skilled in the art and are considered to be within the scope of the present invention. Such techniques are, e.g., described in Tijssen, "Practice and theory of enzyme immuno assays", Burden, R H and von Knippenburg (Eds), Volume 15 (1985), "Basic methods in molecular biology"; Davis L G, Dibmer M D; Battey Elsevier (1990), Mayer et al., (Eds) "Immunochemical methods in cell and molecular biology" Academic Press, London (1987), or in the series "Methods in Enzymology", Academic Press, Inc. There are many different labels and methods of labeling known to those of ordinary skill in the art. Commonly used labels comprise, inter alia, fluorochromes (like fluorescein, rhodamine, Texas Red, etc.), enzymes (like horse radish peroxidase, β-galactosidase, alkaline phosphatase), radioactive isotopes (like $^{32}P$ or $^{125}I$), biotin, digoxygenin, colloidal metals, chemi- or bioluminescent compounds (like dioxetanes, luminol or acridiniums). Labeling procedures, like covalent coupling of enzymes or biotinyl groups, iodinations, phosphorylations, biotinylations, random priming, nick-translations, tailing (using terminal transferases) are well known in the art. Detection methods comprise, but are not limited to, autoradiography, fluorescence microscopy, direct and indirect enzymatic reactions, etc.

In addition, the above-described compounds etc. may be attached to a solid phase. Solid phases are known to those in the art and may comprise polystyrene beads, latex beads, magnetic beads, colloid metal particles, glass and/or silicon chips and surfaces, nitrocellulose strips, membranes, sheets, animal red blood cells, or red blood cell ghosts, duracytes and the walls of wells of a reaction tray, plastic tubes or other test tubes. Suitable methods of immobilizing NCS-1 nucleic acids, (poly)peptides, proteins, antibodies, etc. on solid phases include but are not limited to ionic, hydrophobic, covalent interactions and the like. The solid phase can retain one or more additional receptor(s) which has/have the ability to attract and immobilize the region as defined above. This receptor can comprise a charged substance that is oppositely charged with respect to the reagent itself or to a charged substance conjugated to the capture reagent or the receptor can be any specific binding partner which is immobilized upon (attached to) the solid phase and which is able to immobilize the reagent as defined above.

Commonly used detection assays can comprise radioisotopic or non-radioisotopic methods. These comprise, inter alia, RIA (Radioisotopic Assay) and IRMA (Immune Radioimmunometric Assay), EIA (Enzym Immuno Assay), ELISA (Enzyme Linked Immuno Assay), FIA (Fluorescent Immuno Assay), and CLIA (Chemioluminescent Immune Assay). Other detection methods that are used in the art are those that do not utilize tracer molecules. One prototype of these methods is the agglutination assay, based on the property of a given molecule to bridge at least two particles.

For diagnosis and quantification of (poly)peptides, polynucleotides, etc. in clinical and/or scientific specimens, a variety of immunological methods, as described above as well as molecular biological methods, like nucleic acid hybridization assays, PCR assays or DNA Enzyme Immunoassays (Mantero et al., Clinical Chemistry 37 (1991), 422-429) have been developed and are well known in the art. In this context, it should be noted that the NCS-1 nucleic acid molecules may also comprise PNAs, modified DNA analogs containing amide backbone linkages. Such PNAs are useful, inter alia, as probes for DNA/RNA hybridization.

The above-described compositions may be used for methods for detecting expression of a NCS-1 polynucleotide by detecting the presence of mRNA coding for a NCS-1 (poly) peptide which comprises, for example, obtaining mRNA from cells of a subject and contacting the mRNA so obtained with a probe/primer comprising a nucleic acid molecule capable of specifically hybridizing with a NCS-1 polynucleotide under suitable hybridization conditions, and detecting the presence of mRNA hybridized to the probe/primer.

Further diagnostic methods leading to the detection of nucleic acid molecules in a sample comprise, e.g., polymerase chain reaction (PCR), ligase chain reaction (LCR), Southern blotting in combination with nucleic acid hybridization, comparative genome hybridization (CGH) or representative difference analysis (RDA). These methods for assaying for the presence of nucleic acid molecules are known in the art and can be carried out without any undue experimentation.

Furthermore, the invention comprises methods of detecting the presence of a NCS-1 protein in a sample, for example, a cell sample, which comprises obtaining a cell sample from a subject, contacting said sample with one of the aforementioned antibodies under conditions permitting binding of the antibody to the NCS-1 protein, and detecting the presence of the antibody so bound, for example, using immuno assay techniques such as radioimmunoassay or enzyme immunoassay. Furthermore, one skilled in the art may specifically detect and distinguish polypeptides which are functional NCS-1 proteins from mutated forms which have lost or altered their NCS-1 activity by using an antibody which either specifically recognizes a (poly)peptide which has NCS-1 activity but does not recognize an inactive form thereof or which specifically recognizes an inactive form but not the corresponding polypeptide having NCS-1 activity.

The invention also encompasses a method for diagnosing in a subject a predisposition to a CNS disorder associated with the expression of a NCS-1 allele which comprises isolating DNA from victims of the disorder associated with the under -or over-expression of a NCS-1 protein or a mutant form thereof; digesting the isolated DNA with at least one restriction enzyme; electrophoretically separating the resulting DNA fragments on a sizing gel; contacting the resulting gel with a nucleic acid probe as described above capable of specifically hybridizing to DNA encoding a NCS-1 protein and labeled with a detectable marker; detecting labeled bands on the gel which have hybridized to the labeled probe to create a band pattern specific to the DNA of victims of the disorder associated with the expression of a NCS-1 protein; preparing the subject's DNA according to the above-mentioned steps to produce detectable labeled bands on a gel; and comparing the band pattern specific to the DNA of victims of the disorder associated with the expression of a NCS-1 protein and the subject's DNA to determine whether the patterns are the same or different and to diagnose thereby predisposition to the disorder if the patterns are the same. The detectable markers of the present invention may be labeled with commonly employed radioactive labels, such as, for example, $^{32}P$ and $^{35}S$, although other labels such as biotin or mercury as well as those described above may be employed as well. Various methods well-known to the person skilled in the art may be used to label the detectable markers. For example, DNA sequences and RNA sequences may be labeled with $^{32}P$ or $^{35}S$ using the random primer method. Once a suitable detectable marker has been obtained, various methods well-known to the person skilled in the art may be employed for contacting the detectable marker with the sample of interest. For example, DNA-DNA, RNA-RNA and DNA-RNA hybridizations may be performed using standard procedures. Various methods for the detection of nucleic acids are well-known in the art, e.g., Southern and northern blotting, PCR, primer extension and the like. Suitable further DNA amplification techniques are known in the art and comprise, inter alia, Ligase Chain reaction, Strand Displacement Amplification, Nucleic Acid Sequence based Amplification (NASBA), or Q-beta replicase.

Furthermore, the mRNA, cRNA, cDNA or genomic DNA obtained from the subject may be sequenced to identify mutations which may be characteristic fingerprints of NCS-1 mutations in CNS disorders such as described above associated with the expression of NCS-1 or mutated versions thereof. The present invention further comprises methods, wherein such a fingerprint may be generated by RFLPs or AFLP of DNA or RNA obtained from the subject, optionally the DNA or RNA may be amplified prior to analysis, the methods of which are well known in the art. RNA fingerprints may be performed by, for example, digesting an RNA sample obtained from the subject with a suitable RNA-Enzyme, for example RNase $T_1$, RNase $T_2$ or the like or a ribozyme and, for example, electrophoretically separating and detecting the RNA fragments on PAGE as described above. Preferably, hybridization (and subsequent washing) is effected under stringent conditions; see, e.g., Sambrook et al., loc. cit and supra.

Furthermore, the present invention relates to a method as described above wherein said sample is or is derived from hair, blood, serum, sputum, feces or another body fluid. The sample to be analyzed may be treated such as to extract, inter alia, nucleic acid molecules, (poly)peptides, or antibodies.

The present invention also relates to kit compositions containing NCS-1 specific reagents such as those described herein-before. Kits containing NCS-1 DNA or RNA, antibodies to NCS-1, or NCS-1 protein may be prepared. Such kits are used to detect DNA which hybridizes to NCS-1 nucleic acid or to detect the presence of NCS-1 protein or peptide fragments in a sample. Such characterization is useful for a variety of purposes including but not limited to forensic analyses, diagnostic applications, and epidemiological studies in accordance with the above-described methods of the present invention.

The recombinant NCS-1 proteins, DNA molecules, RNA molecules and antibodies lend themselves to the formulation of kits suitable for the detection and typing of NCS-1. Such a kit would typically comprise a compartmentalized carrier suitable to hold in close confinement at least one container. The carrier would further comprise reagents such as recombinant NCS-1 protein or anti-NCS-1 antibodies suitable for detecting NCS-1. The carrier may also contain a means for detection such as labeled antigen or enzyme substrates or the like.

These and other embodiments are disclosed and encompassed by the description and Examples of the present invention. Further literature concerning any one of the antibodies, methods, uses and compounds to be employed in accordance with the present invention may be retrieved from public libraries and databases, using for example electronic devices. For example the public database "Medline" may be utilized which is available on the Internet. Further databases and addresses are known to the person skilled in the art. An overview of patent information in biotechnology and a survey of relevant sources of patent information useful for retrospective searching and for current awareness is given in Berks, TIBTECH 12 (1994), 352-364.

This disclosure may best be understood in conjunction with the accompanying drawings, incorporated herein by references. Furthermore, a better understanding of the present invention and of its many advantages will be had from the following examples, given by way of illustration and are not intended as limiting.

Unless stated otherwise in the examples, all recombinant DNA techniques are performed according to protocols as described in Sambrook et al. (1989), Molecular Cloning: A Laboratory Manual. Cold Spring Harbor Laboratory Press, NY or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, jointly published by BIOS Scientific Publications Ltd (UK) and Blackwell Scientific Publications (UK). Site-directed mutagenesis was performed using the QuikChange Site-directed Mutagenesis kit (Stratagene). Wild-type C. elegans Bristol strain (N2) was obtained from the Caenorhabditis Genetics Center (funded by the NIH National Center for Research Resources).

The Figures show:

FIG. 1. Expression pattern of the ncs-1::GFP reporter gene (A) ncs-1 gene expression is observed in amphid, phasmid, nerve ring, and ventral nerve cord of L1 stage animals as GFP staining. Scale bar: 100 μM.

(B) ncs-1 gene expression in adult head showing GFP staining in amphid dendrites. Scale bar: 10 μM.

Figure 2:
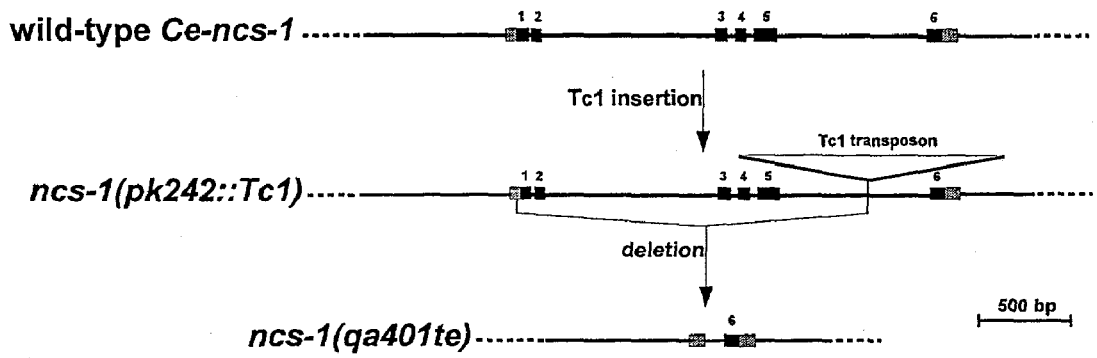
Figure 2:
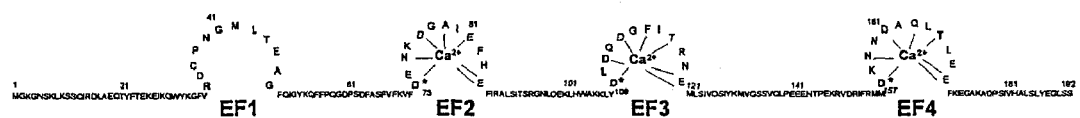
Figure 2:
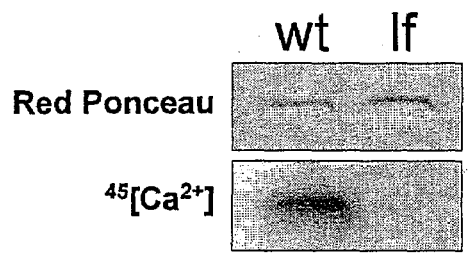
Figure 2:
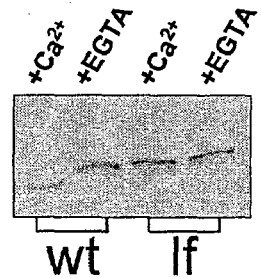

FIG. 2. Ce-NCS-1: from gene structure to calcium sensor (A) Physical maps of wild-type Ce-ncs-1, ncs-1(pk242::Tc1), and null ncs-1(qa401te) deletion genes. Black boxes represent exons 1-6, and the gray boxes the 5' and 3' untranslated regions of the ncs-1 gene. Scale bar: 500 base pairs.

(B) The NCS-1 protein contains 4 EF-hands (EF1-4), but the first binding site is degenerated and cannot bind $Ca^{2+}$ (De Castro et al., 1995). The amino acid sequence for the NCS-1 protein containing 4 EF-hands is provided in SEQ ID NO: 5. The Asp positions D73, D109, and D157 are essential for calcium binding. Changing the three Asp residues (D*) into Ala inactivates $Ca^{2+}$ binding (Putkey et al., 1989) (see below).

(C) The loss-of-function (lf) triple mutant was constructed by substituting the first Asp (D*) residue to an Ala of the three EF-hands EF2, 3 and 4.

(D) Ce-NCS-1 is a calcium sensor. Calcium bound wild-type NCS-1 displayed a greater electrophoretic mobility than the apo form, whereas lf-NCS-1 mobility was not affected by the presence ($+Ca^{2+}$) or absence (+EGTA) of free calcium. It suggests that $Ca^{2+}$ induces an allosteric change in the conformation and probably activity of Ce-NCS-1.

Figure 3:
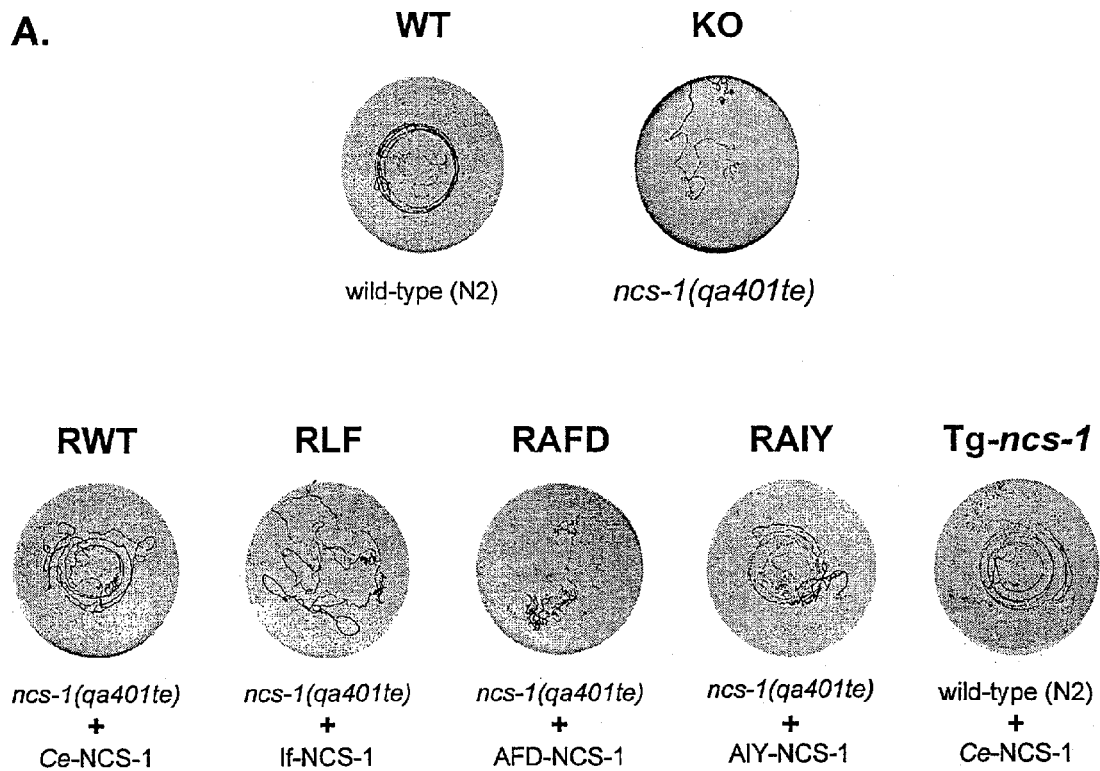
Figure 3:
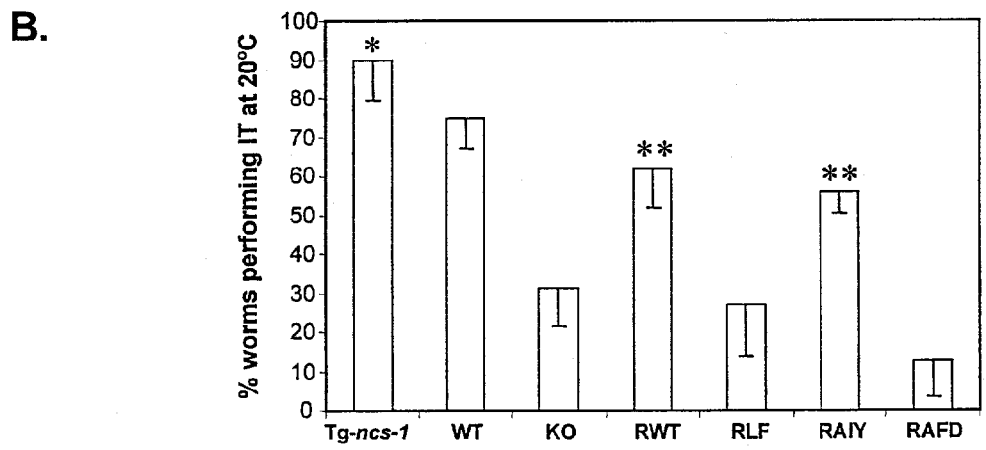
Figure 3:
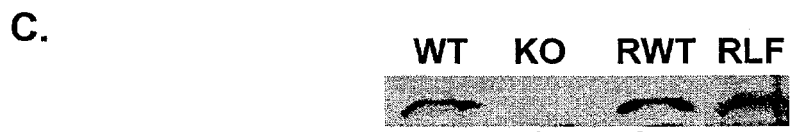

FIG. 3. $Ca^{2+}$ signaling via NCS-1 in the AIY interneuron is essential for isothermal tracking behavior (A) Individual isothermal tracking (IT) records. Photographs of normal or disrupted isothermal behavior tracks of wild-type (WT), ncs-1(qa401te) knockout (KO), rescued ncs-1(qa401te) with wild-type ncs-1 (RWT), or with loss-of-function ncs-1 (RLF), or with AFD neuron specific promotor (RAFD) driving the expression of NCS-1, or with AIY neuron specific promotor (RAIY) driving the expression of NCS-1, and wild-type plus transgenic ncs-1 (Tg-ncs-1) individual worms are shown. Thermotaxis assays were performed as described in (Mori and Ohshima, 1995).

(B) Percentage (group performance) of worms performing IT behavior after overnight feeding at 20° C. Each data point represents 4-10 independent assays using approximately 10-20 animals per assay. At least 2-3 different lines were generated for each transgene construct. The chi-square distribution and T-test were used to determine the significance of IT behavior performance between the different strains. The P value (*≦0.02) indicates a significant difference between Tg-ncs-1 animals as compared to wild-type worms. The P values (**≦0.002) represent significant differences of performance between KO animals and RWT or RAIY worms. For these experiments, standard deviations range from 7 to 14%. A trace is considered as isothermal if more than half of the trace length left on the agar surface by a single animal is circular or present an arc of circle near the isotherm of the growth temperature.

(C) Ce-NCS-1 protein levels in the various WT, KO, RWT, RLF strains or lines. Western blot analysis using Ce-NCS-1 polyclonal antibodies and 80 µg of total protein extract reveals the presence of the NCS-1 calcium sensor in the wild-type strain (WT), in the NCS-1 rescued wild-type lines (RWT), and in the rescue loss-of-function lines (RLF). Note the absence of NCS-1 in the knockout strain (KO).

Figure 4:
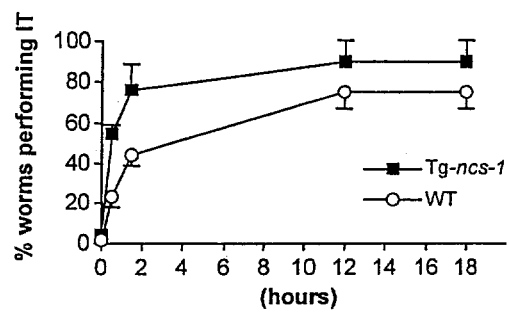
Figure 4:
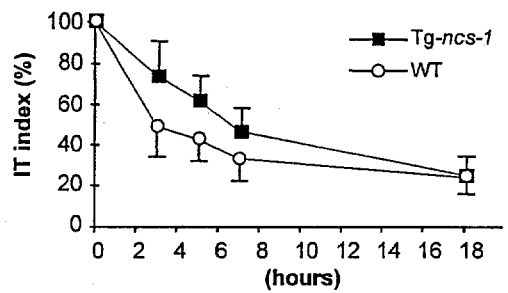

FIG. 4. Faster acquisition (learning) and longer retention (memory) for NCS-1 overexpressing worms (A) The acquisition of the association of food at a given temperature was determined for wild-type (WT) and overexpressing NCS-1 (Tg-ncs-1) worms by measuring the % of worms performing IT behavior at 20° C. Briefly, worms were grown on seeded plates at 25° C. for at least 12 hours, then shifted individually to a seeded plate at 20° C. for different time intervals. For both strains, the maximal levels of IT behavior (absolute values) were reached after pairing the conditioning stimuli for at least 12 hours. 50% of the maximum level was reached after 68 minutes for WT worms, and after only 28 minutes with Tg-ncs-1 worms. As the half-maximal acquisition was scored instead of the relative IT index (see definition below), the experiment was internally controlled for increased performance for each strain.

(B) The extinction of this association (food at 20° C.) was determined for wild-type (WT) and overexpressing NCS-1 (Tg-ncs-1) worms. Briefly, worms were grown at 20° C. in presence of food for at least 18 hours, washed at 20° C., and transferred to unseeded plate at 20° C. for different time intervals. Normalized IT values (IT index) were used to correct for the increased performance of Tg-ncs-1 worms after conditioning, and to only consider extinction of trained animals. 100% correspond to the mean performance achieved after 18 hours at 20° C. (see FIG. 4A for absolute values). Half maximal extinction was obtained after 3 hours with WT worms, whereas Tg-ncs-1 worms had a prolonged retention, and reached half-maximal extinction after about 7 hours.

Figure 5:
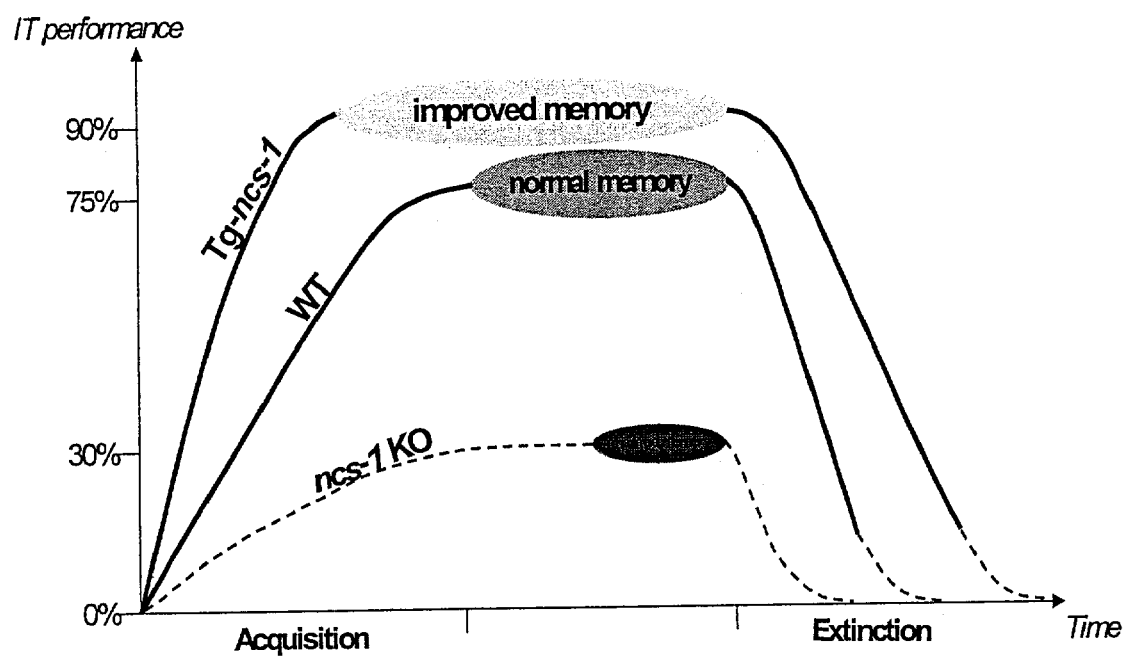

FIG. 5. Regulation of associative learning and memory by NCS-1

The schematic view indicates that the amount of NCS-1 directly regulates IT behavior. The absence of the neuronal calcium sensor-1 (ncs-1 KO) impedes the majority of worms from performing isothermal tracking behavior, whereas its presence (WT) allows it. Overexpression of NCS-1 (Tg-ncs-1) enhances performance levels, accelerates learning, and produces a memory with slower extinction. Slower extinction might reflect increased responsiveness of the AIY integrative neurons to $[Ca^{2+}]_i$ stimuli. The amount of NCS-1 in the AIY neurons and the strength of $Ca^{2+}$ stimulation are linked together to modulate associative learning and memory in *C. elegans*. The dotted lines represent hypothetical IT responses.

Figure 6:
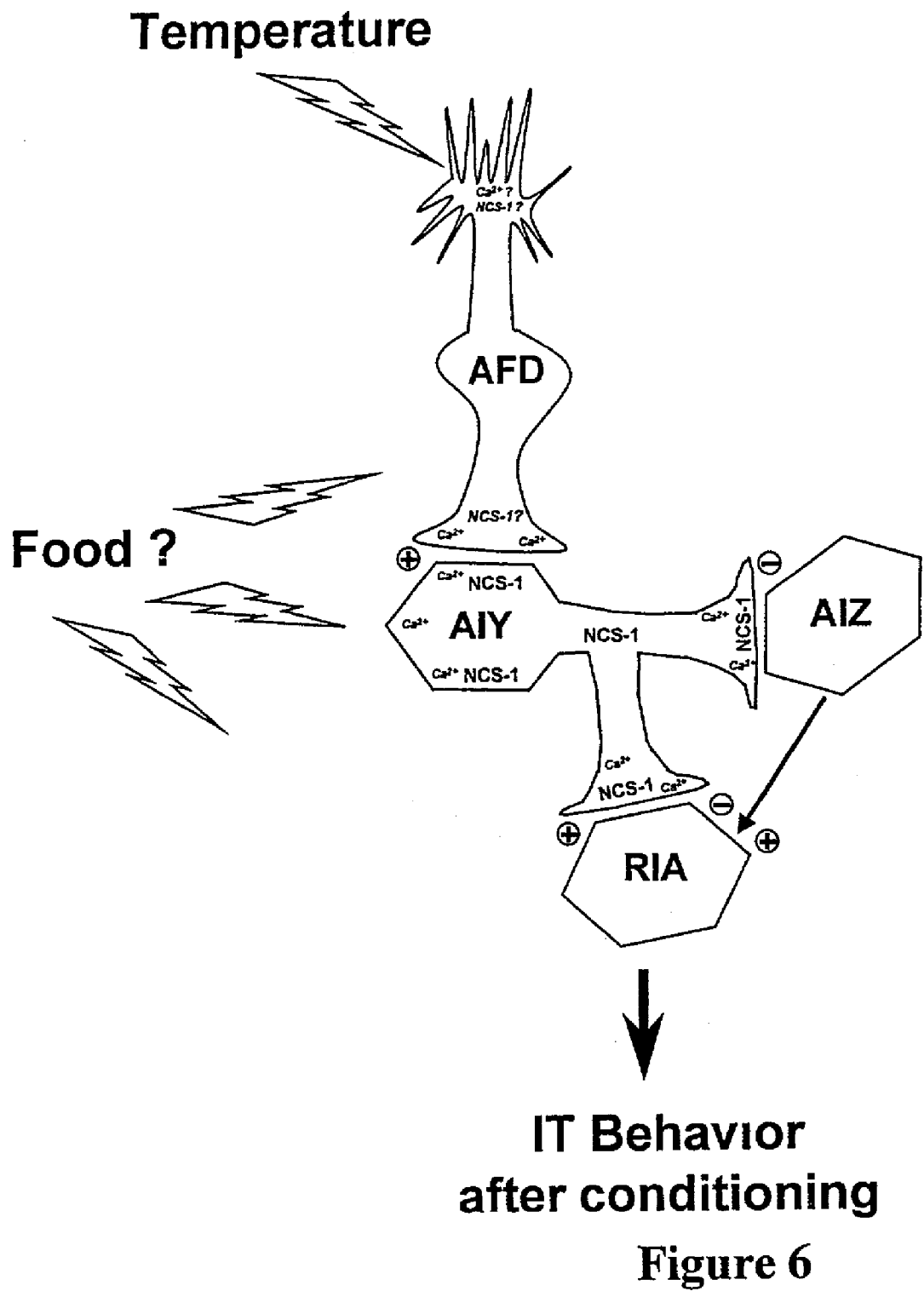

FIG. 6. Model for a pre or postsynaptic role of the neuronal calcium sensor-1

NCS-1 is present in the AFD and AIY neurons, either at the dendritic or axonal terminals, and its function in the AIY neurons is essential for IT behavior. In this model, the AIY interneuron serves as an integrator of food and temperature inputs, and the NCS-1 calcium sensor transduces calcium signals and regulates synaptic strength between AIY/AIZ and AIY/RIA cells at the presynaptic location, or between AFD/AIY neurons in a postsynaptic location. The + or − sign indicates the presence of an excitatory or inhibitory synapse.

Figure 7:
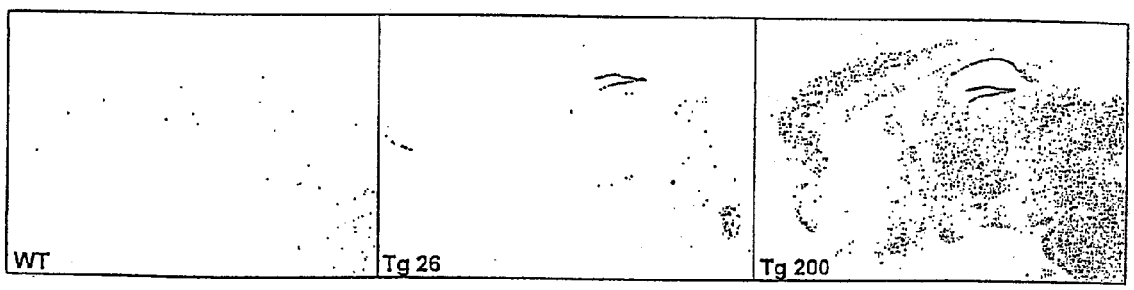
Figure 7:
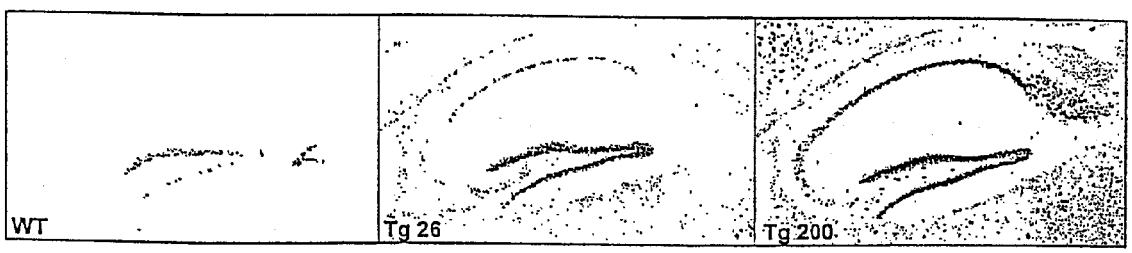
Figure 7:
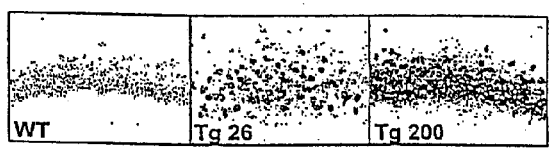
Figure 7:
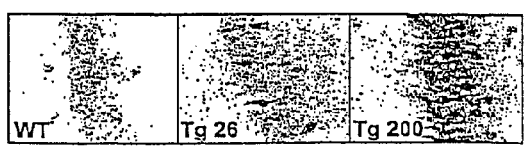
Figure 7:
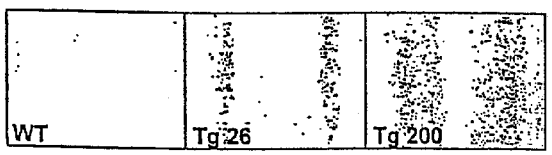
Figure 7:
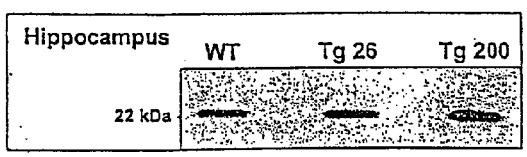

FIG. 7. Expression of the thy1::ncs-1 transgene in lines Tg 26 and Tg 200

(A) In situ hybridization using a digoxigenin-labelled cRNA antisense probe complementary to the 3'UTR of the chick NCS-1 (cNCS-1) transgene. Strong signals are observed in parasagital sections from mouse transgenic lines Tg26 and Tg200 (see Table II for a detailed description of cNCS-1 distribution). Tg26 is characterized by an overexpression of NCS-1 in hippocampus and spinal cord, whereas Tg200 has a quantitatively and spatially broader brain distribution for the cNCS-1 transgene.

(B) Overexpression of cNCS-1 in the hippocampus of Tg26 and Tg200. Enlargement of the section shown in (A). Note the highest amount of cNCS-1 transcripts in Tg200. Microscope views of the CA1 (C) and CA3 regions (D).

(E) No signal is observed in lumbar spinal cord slices prepared from WT littermates whereas Tg26 and Tg200 animals show strong cNCS-1 hybridization signals. (F) Total NCS-1 protein level in WT, Tg26 and Tg200 lines. Western blot analysis using 30 µg of total hippocampal protein extracts and a polyclonal antibody against human NCS-1 reveals a significant increase in the level of NCS-1 in Tg26 (2 fold), and in Tg200 (6 fold) as compared to WT.

Figure 8:
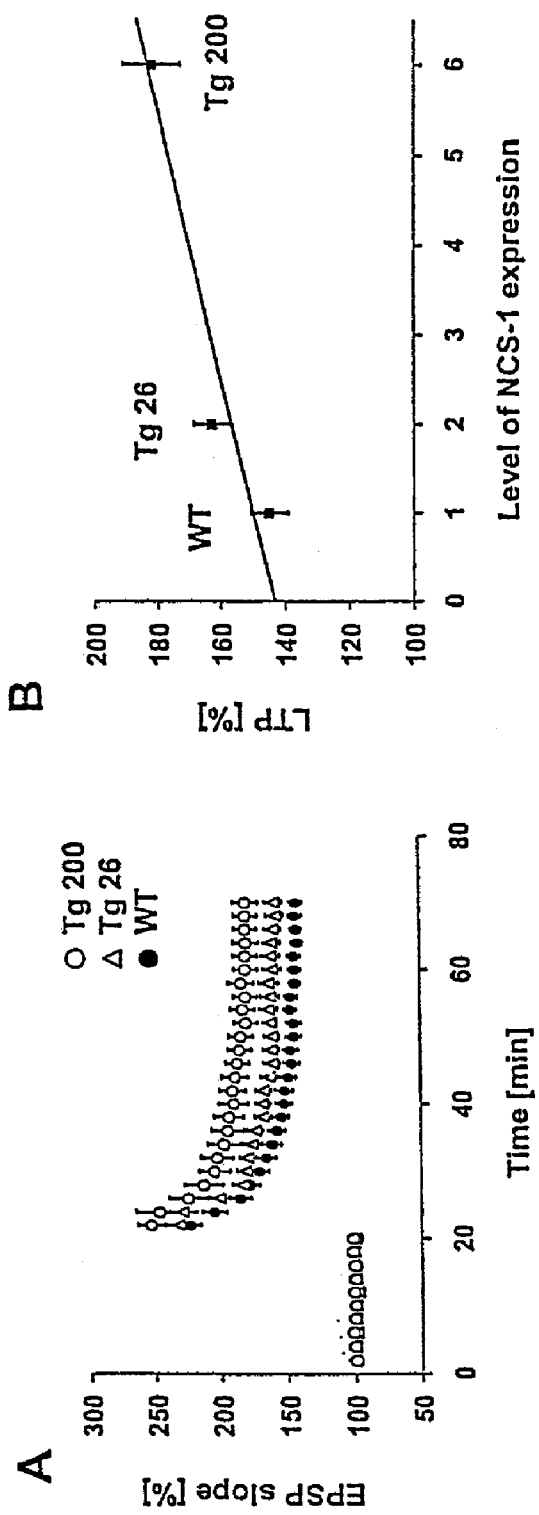

FIG. 8. Enhancement of LTP in area CA1 is NCS-1 dose dependent (A) Changes in EPSP slope induced by theta-burst patterned stimulation in slices prepared from WT (n=4), Tg26 (n=4) and Tg200 (n=4) animals. The LTP level obtained 30 min after stimulation is 181.81%+/−9.1 (n=13) for Tg200, 162.62%+/−5.73 (n=13) Tg26, and 144.96+/−5.75 (n=41) for WT. The LTP enhancement produced by NCS-1 overexpression is larger in Tg200 than in Tg26, and WT, and is statistically significant between Tg200 and WT ($p<0.006$), between Tg26 and WT or between Tg200 and Tg26 ($p<0.03$). Note that LTP is enhanced from the onset and lasts at least 70 min under these experimental conditions.

(B) Correlation between NCS-1 and LTP enhancement levels in area CA1 30 min after the initial stimulation. There is a strong correlation between the amount of NCS-1 and the resulting LTP. The highest level of NCS-1 produces a larger LTP increase.

Figure 9:
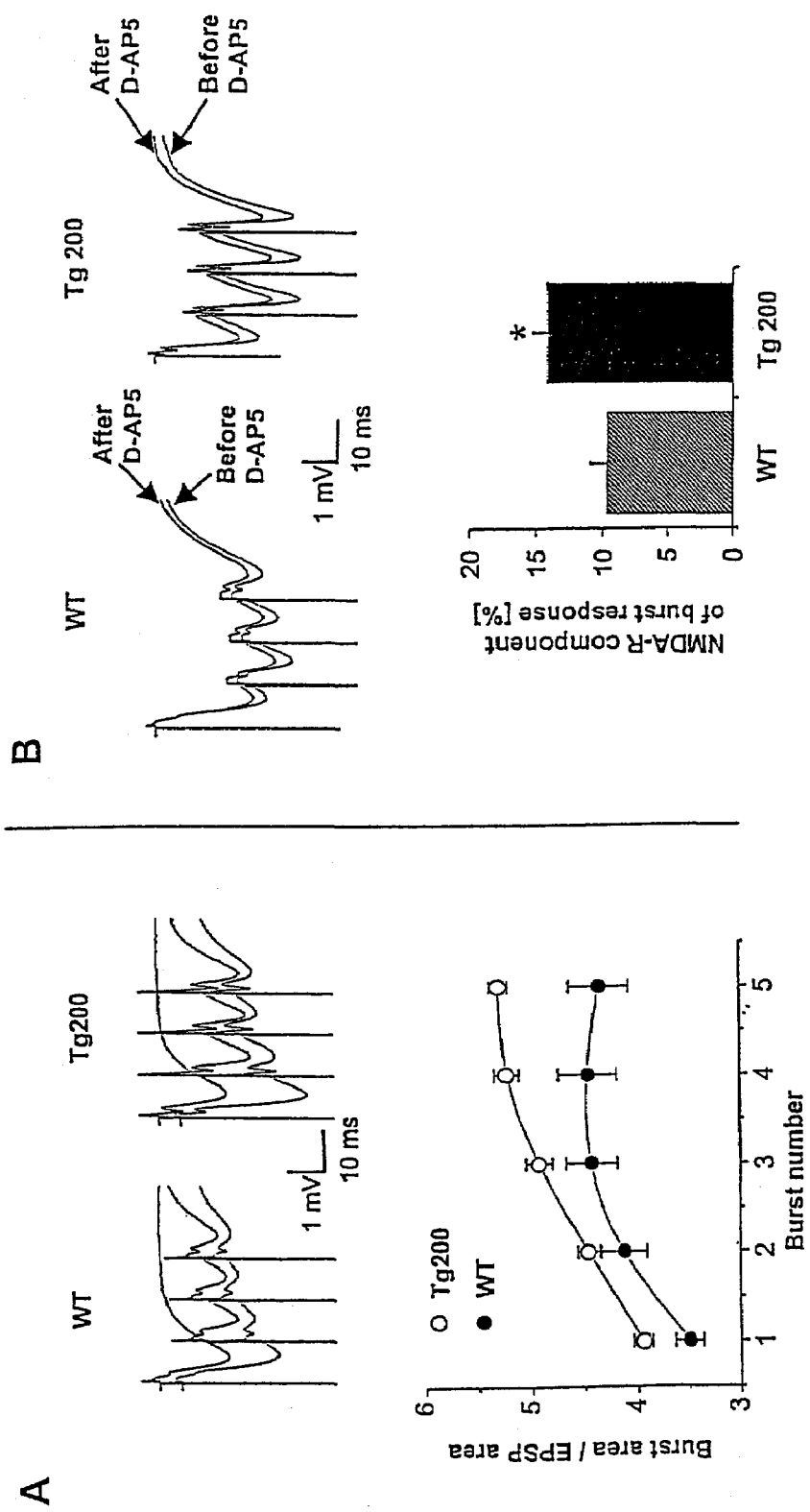

FIG. 9. Overexpression of NCS-1 enhances the NMDA receptor component of burst responses (A) Enhancement of the summation of responses during the trains used to induced LTP. Upper panel: the traces represent responses elicited by a single stimulation or by the first and fifth train used to induce LTP in Tg200 and WT slices. The fifth train is shown slightly shifted for convenience. Lower panel: area under the burst responses expressed for each train as percent of the area under the EPSP evoked by a single stimulation in Tg200 and WT slices. Overexpression of NCS-1 results in larger responses during the trains that further increase with the number of bursts.

(B) Upper panel: primed burst responses of the type used to induce LTP recorded before and after application of the NMDAR antagonist D-AP5 at 50 µM. Each trace is the mean of four consecutive records, and the difference between the two records reflects the NMDA-receptor dependent component of burst responses. Lower panel: size of the NMDA receptor component of burst responses expressed as percent of the area under the burst EPSP in slices prepared from Tg200 mice (black column, n=9) and WT mice (dashed column, n=8, p<0.05).

Figure 10:
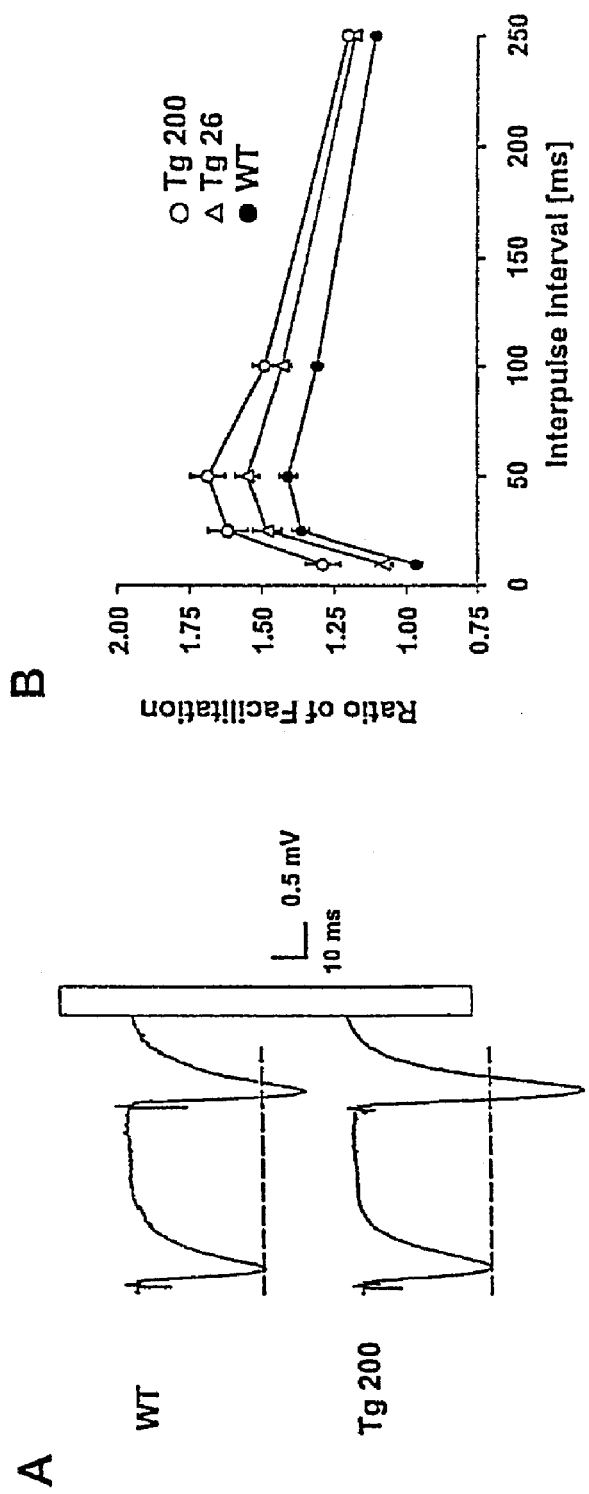

FIG. 10. Enhancement of paired-pulse facilitation by NCS-1 is dose-dependent (A)

Paired-pulse responses elicited at 50 ms interpulse interval in area CA1 of slices from WT and Tg200 animals. The horizontal dotted line shows, for comparison, the maximum amplitude of the first EPSP. Note the enhanced facilitation in Tg200 slices. Scales are indicated. (B) Degree of facilitation (mean+/−SEM) obtained in hippocampal slices from WT (n=14), Tg26 (n=7) and Tg200 (n=5) mice and calculated for various interpulse intervals as the ratio of the amplitude of the second over the first response elicited by a paired stimulation. Differences are statistically significant for interpulse intervals of 20-250 ms between WT and Tg26/Tg200, and for interpulses of 20-100 ms between Tg26 and Tg200. The enhancement of paired-pulse facilitation is NCS-1 dose-dependent.

Figure 11:
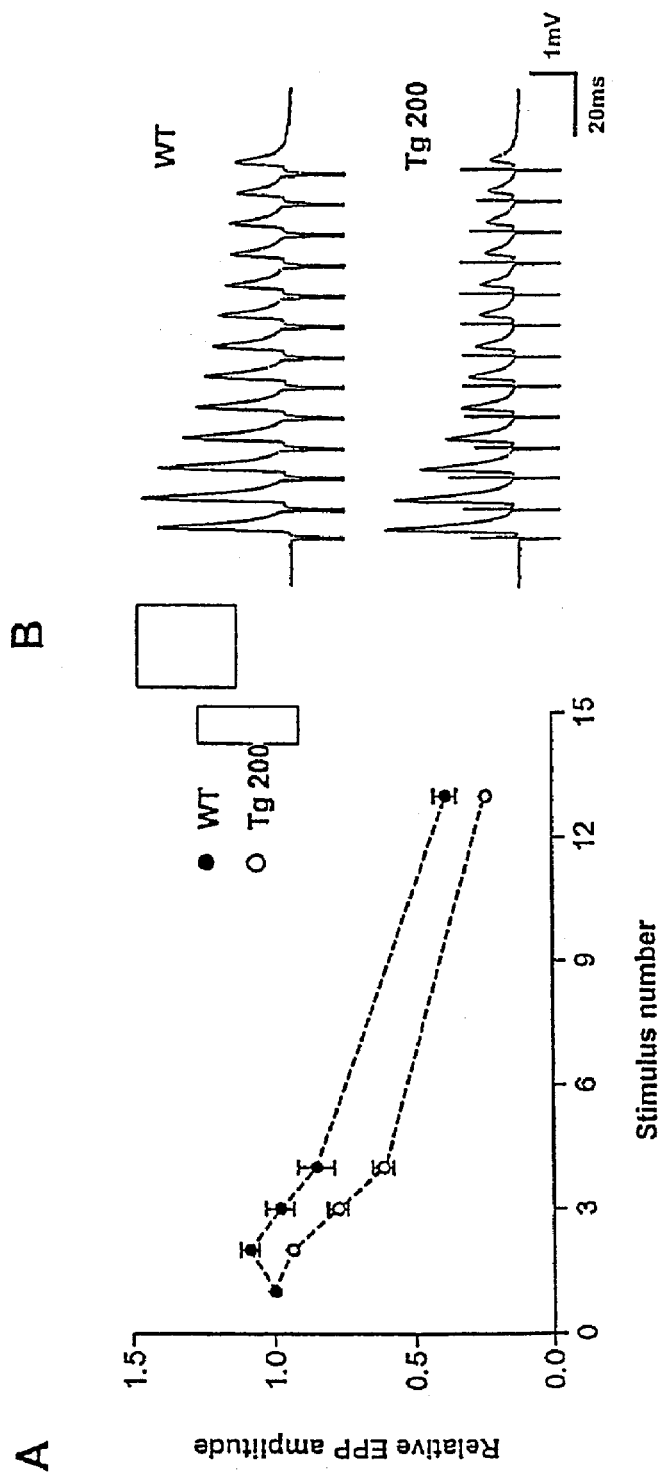

FIG. 11. Enhancement of neurotransmitter release at the neuromuscular junction by cNCS-1

Experiments with the left hemidiaphragm muscles of Tg200and WT are shown. Relative end plate potential (EPPs) (means+/−SEM; n=4 muscles) in 100 Hz trains of 13 stimuli, are applied once every 6 seconds, and 5-12 endplates are analyzed per muscle with an average of 10-30 pulse trains per endplate. (A) Normalized data shows a significant increase of synaptic fatigue with Tg200, which is also observed (data not shown) by an increase of extracellular $Ca^{2+}$. Therefore, enhanced neurotransmitter quanta release during initial stimuli create a depletion in the pool of "ready to be secreted" transmitter vesicles for the subsequent action potentials (fatigue). (B) Illustration of averaged endplate potentials from a WT and a transgenic endplate. Scale is indicated.

Figure 12:
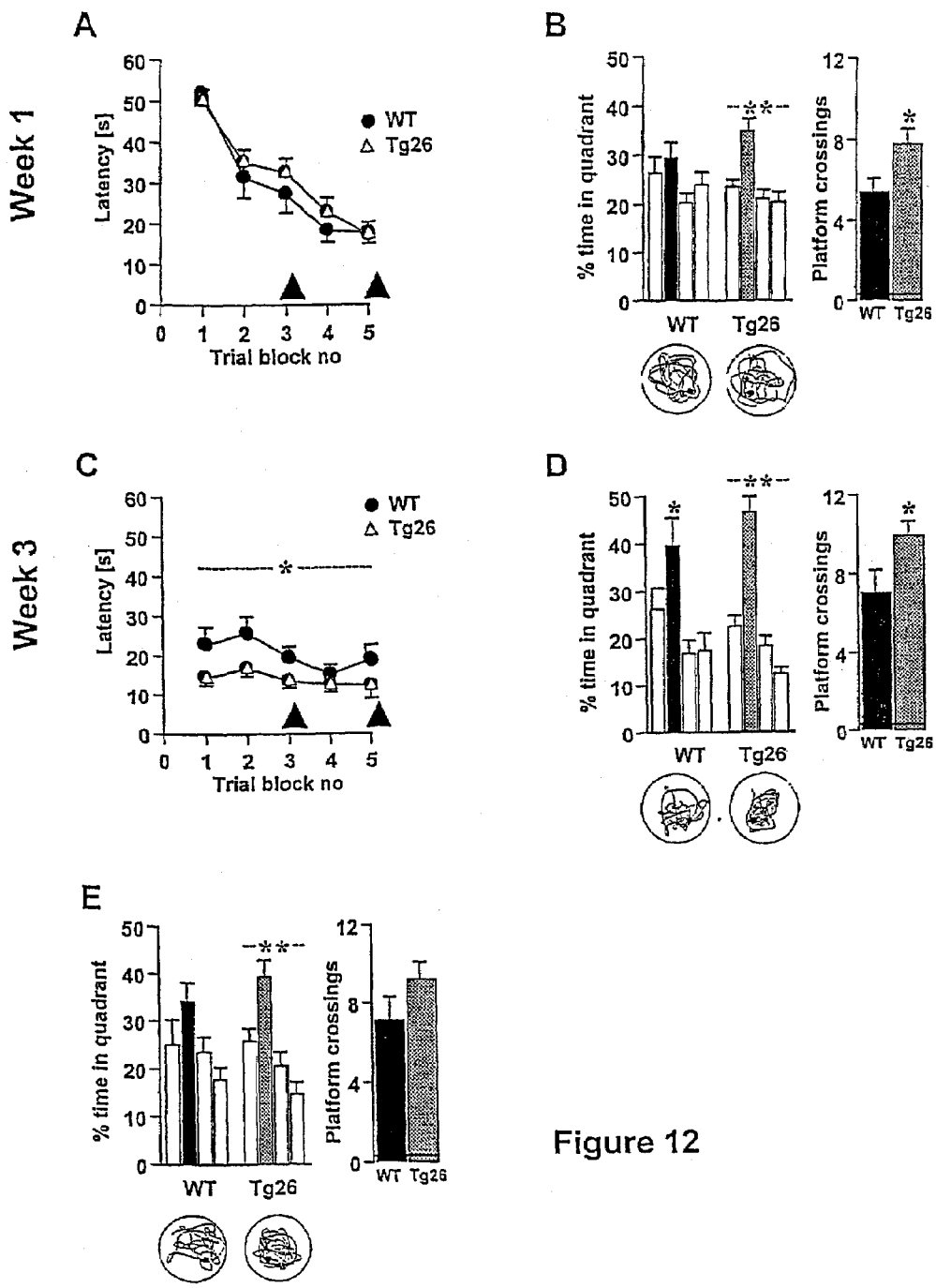

FIG. 12. Spatial memory in Morris water maze task is improved in the NCS-1 overexpressing line Tg26

(A and C) Comparison between Tg26 line and WT littermate controls on the acquisition of spatial water maze learning for a hidden platform using a spaced trials procedure (3 trials/day, 10 min ITI). No significant difference in latency (F1, 18=1.0, NS) or swim speed (F1, 18=2.3, NS) was recorded (Week 1). After a seven day interval, a second spaced trials procedure was conducted (Week 3), identical in design to Week 1. In this study phase, a main effect of group on latency factor was noted (F1, 18=4.8, p<0.05). (B) Probe tests were conducted after trial blocks 3 and 5 in each study phase as indicated by the filled triangles. Neither group showed any spatial bias after trial block 3 (data not shown) on Week 1, however by trial block 5, the Tg26 line had developed a significant island quadrant preference (Tg26 line: F3,27=9.3, p<0.01; WT: F3,27=1.5, NS). Furthermore Tg26 mice made significantly more island crossings reflecting greater accuracy of search. The median path plots for each group are also presented.

(D) Probe tests performed during Week 3, revealed improved performance of the Tg26 line on each occasion, e.g. the data represent performance for the probe test conducted after trial block 5, where the Tg26 line made more island crossings and had greater spatial preference for the island quadrant compared to controls. After trial block 3 only the Tg26 line had a significant preference for the island quadrant (Tg26 line: F3,27=11.4, p<0.01; WT: F3,27=1.3, NS; island crossings: Tg26 9.2±1.0, WT 5.4±0.8, p<0.01). (E) Probe test conducted 5 days after Week 3, again indicated an improved spatial recall for the island platform location in the Tg26 line (Tg26 line: F3,27=11.1, p<0.01; WT: F3,27=2.1, NS).

Figure 13:
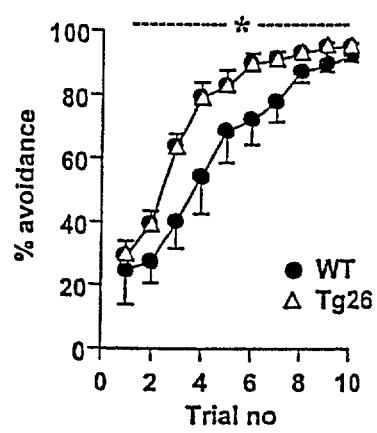
Figure 13:
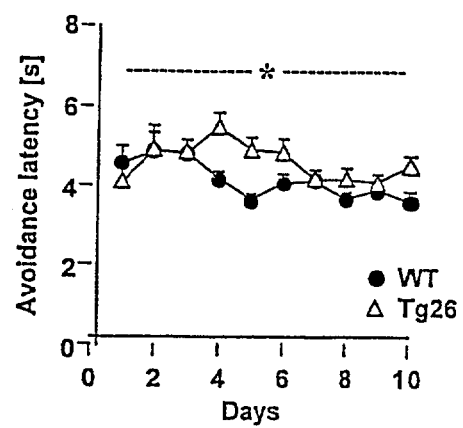

FIG. 13. Improved associative memory (active avoidance) with the NCS-1 overexpressing line Tg26

(A) Active avoidance learning, with the Tg26 line showing increased acquisition compared to WT (genotype×trial block interaction F9, 198=1.9 p<0.05). (B) The Tg26 line also demonstrated significantly lower avoidance latencies (strain effect F1, 19=11.9, p<0.05) although escape latencies were similar between groups (genotype×trial block interaction F9,81=0.8, p>0.05).

Figure 14:
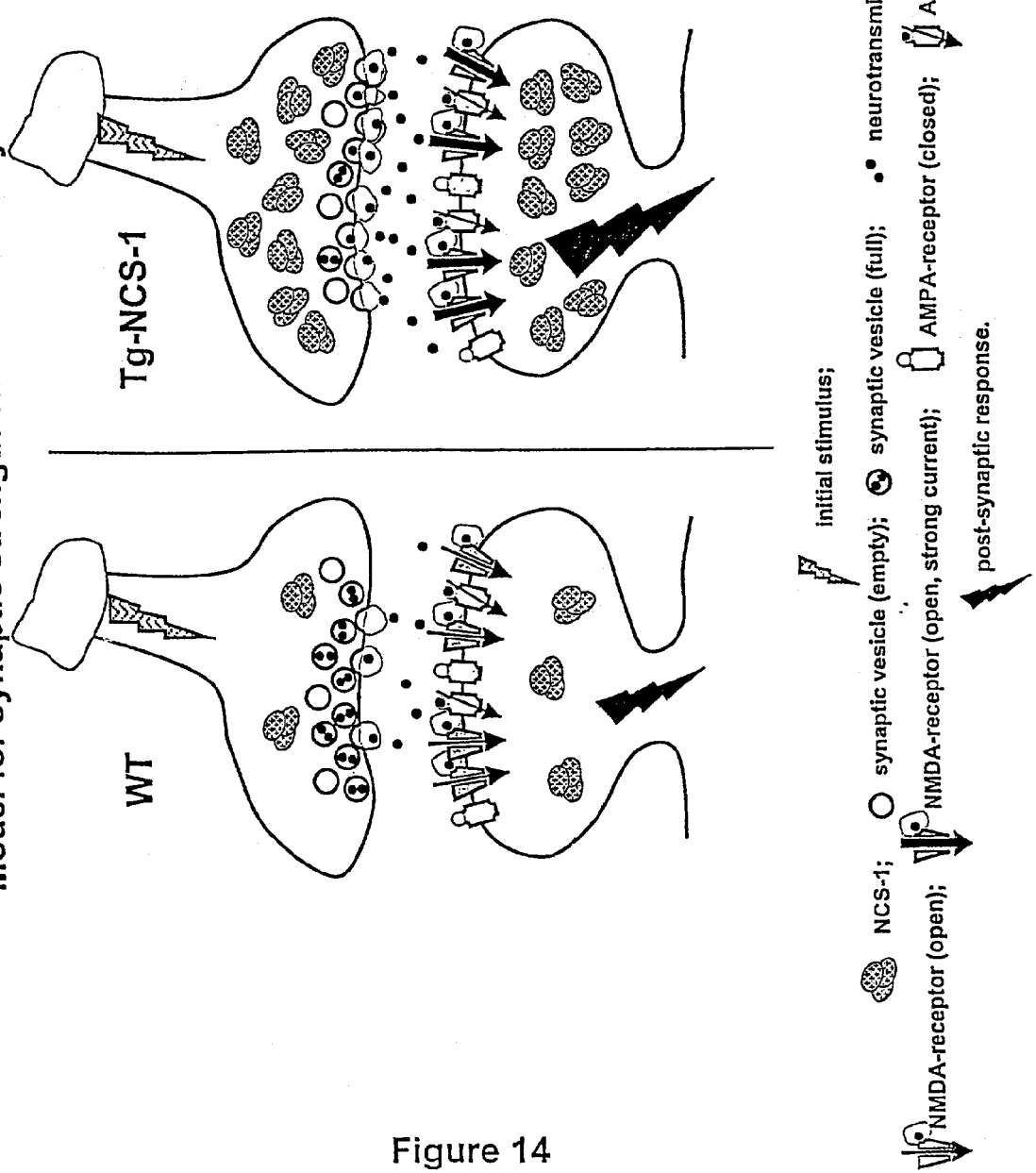

FIG. 14. Model for synaptic strength enhancement by NCS-1 overexpression

NCS-1 is overexpressed on both ends of the synapse in transgenic mice line Tg26 and Tg200. In this model the neuronal calcium sensor 1, serves as a dose-dependent synaptic vesicle release modulator where the amount of presynaptic NCS-1 proportionally influences the probability of neurotransmitter release. The more NCS-1, the more neurotransmitter are released. As a result of the NCS-1 modulation effect, the postsynaptic depolarization is enhanced, more AMPA receptors are opened, more NMDA receptors are opened, and the final output signal is increased.

Figure 15:
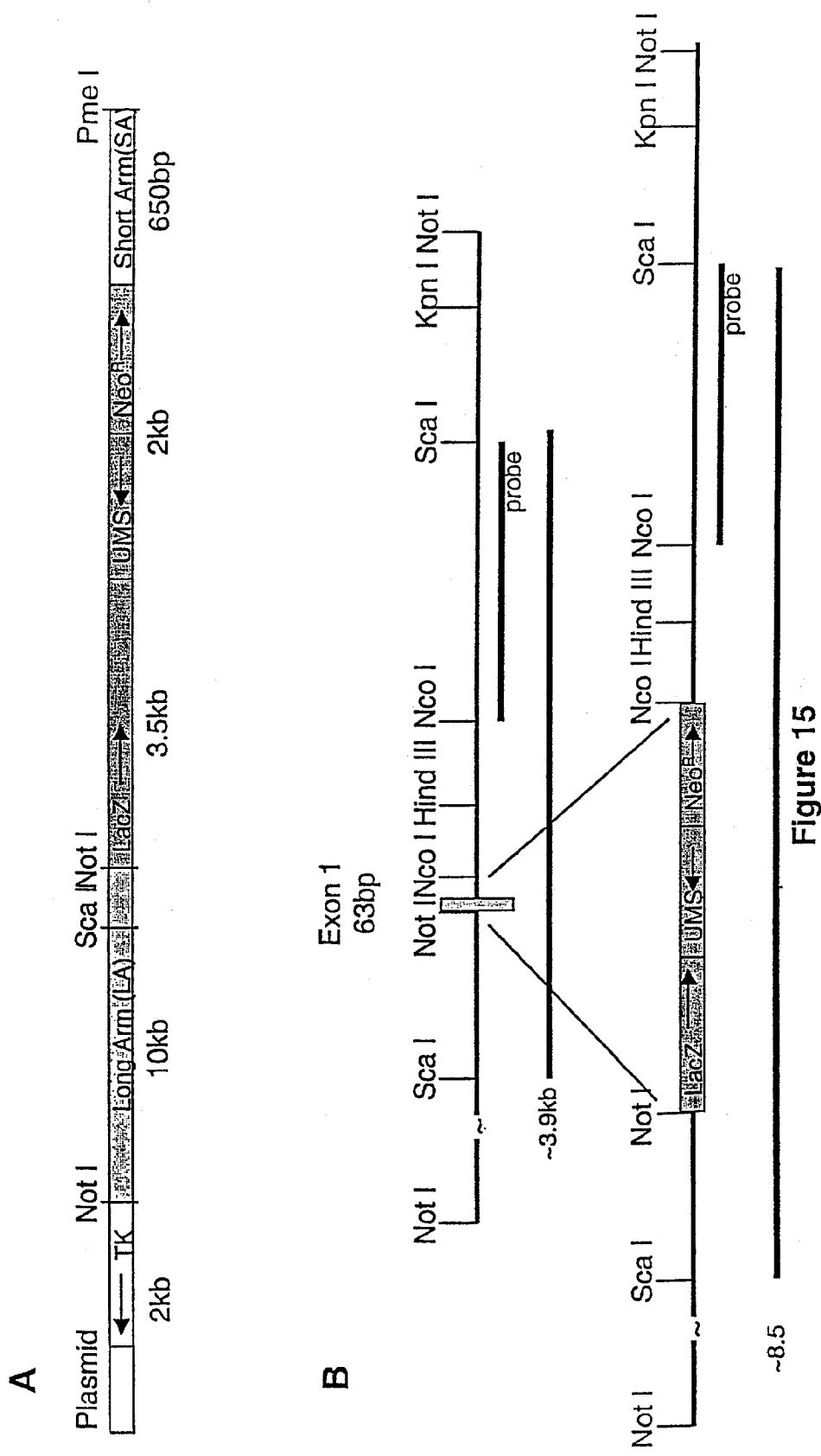

FIG. 15. Targeting construct and analysis methods for NCS-1 knock-out mice (A) Targeting construct for NCS-1 knock-out mice. (B) Method of targeting and analysis of homologous recombination with probes for Southern blot. (C) PCR positive control construct. (D) Targeting method and PCR analysis of homologous recombination.

EXAMPLES

Example 1

Ce-ncs-1 Gene Expression

The Ce-ncs-1 gene, located on the left arm of chromosome X, encodes Ce-NCS-1, a small acidic protein composed of 192 amino acids (molecular mass of 22 kDa) that binds 3 calcium ions via 4 putative EF-hands (De Castro et al., 1995). Cellular distribution of Ce-NCS-1 was determined by light and immunofluorescence microscopy studies using a transgenic line (XA411) expressing the green fluorescent protein (GFP) under the control of the Ce-ncs-1 promoter region (SEQ ID NO: 1).

The ncs-1: GFP reporter gene was constructed by subcloning a ncs-1 3100 bp promotor comprising the sequence of the ncs-1 promoter region:

```
agctttactgtttttgaactaatcatcaattagctccacctacttttaactagatctgttaaca    (SEQ ID NO:1)

acccatgtagtgatagcttccctcattttcaaaccaatcagcagttaggtcaatctatttctaa accaatgagcaactgactccgcctgttgtgaaccaatcaacaaattagctctgccttttttgaa aaaatcaataatttgccttgaccagcagaggaaagaaaagcgacgttaatagctgattaatctt
```

-continued

```
gctacacggaacacggaacaaatttcaagaaagtatattctatcaataaaaaaactattacttt
gtaccgagtattgtgaaaaatcatgaatttctgtaaatgtttaatttgtagaaacatgatctgt
cgccgaaatctgcgcgaaagttgtgtggatcattatttcgttaagtggaaacatgatctatttg
ctcttttttgatgaaagaaacattcccaattatctgggttttcctgaaaacttttcagtctatg
ttactgctgttttaatttaatcttttactggaagtcacgtttaaaattggtttaaagattttat
tcaattttataagatttaaaaaaattgtaggttgaaaattttcagtcagagcttcgaaaagttt
gggataccgtatatcctctattagtaaggcgccgttattagttttgcacctccattagttttgc
atcaaattaggtgtccgaaaattagttttgcataccttactaatagaggaaatacgttttcgtt
tgctccaatttttgttttttttttataaggacagagtaatttctatttttttcgtattccaa
taattaaaatataatcagaaaaataaaatcgtaaaaaataatatgttacgtagacactcacaat
caggtaggcacaacgcatttgggtaatcttctgggcaaagtttgatgcattttcccaacccag
ataaaagtaaaaaaaaacatctaaaaaagtatcaatccccaaaaaaattttgatcattttccag
agctttgctctctttaaaactgcttttgatttcttattcacgtgaaacaattgatgttgctcc
gatgcacaatgtgaacttttgagggttttctgagccattagccactgacccaaaatgtgcagtc
tggaagatattaatttttgcttttttctagaagttttcttgcagtgtttgaaagttttaaga
cctctcatttgccatcttactattagtggaatttcttcaaggaatttctcaatttcaaattcct
actgactggctgttttcaaaaaattacacatcatagttttaatgaaaaatcataggtttaatca
tagttgtaatggaaaaaaccaggtatattacacaagcacccaaaaaaattccagcagtggcttg
gttatggcgatttccggcaatcggtcattgaccgttttcagaaaataggtttgtcacctaaaaa
ttctaatcaggtaataataatagatttcgtgataggggataattcttaatagtaaactttaaaa
tatttttttctctttcaatgatatgacagattcatcttgatttccggttttgtttaagatctga
ataattccaaaaacattcatagctttgatattggttagttgtgacttagcacccaaaaataatt
tactttagcagttttaattcaaaataaaataattctgcgtaaaatttctaaattttcaactttt
ttatcaagattttgtcgagtaatgctacttcatcaaaacttcttactccatcggttgctccgac
tttcttccaatccaaaacatgtaaactcaactatcttttctctattttagagtcctccaaaac
catatgtctgtttgcgcgtgcgtgagatattttccccctttatgcacactcattttgtggttat
tcataaaaatgaaatatacatctagagagaaaagttagagagtcgtagagaaaatagaaattgt
attgcaccatgattttgtcttcttttttgccttcccttggagcaaaatcgctaatcctagct
acgccagtgattgggttgctatggatctcgtgcacacttgctctcatgtacatatgtattttct
cacatattcggttttcccctttttttgatatctatatactgccggccgccgtgcacctcattt
tctctcctcgctccgcacaccatttctgtgtgcctctgacggataaactgatgggcatccggag
cttactggtgacgtttgaggcggctcttctcccctataggaagtttggaattatggccttgagt
gactggaaaaagaagagataactcgcataaacttcatatttccccttcattttgctcatcaaa
tttttgcccttattttaccagagatttgcagaagaactagttagttacgatgatggaacaaaat
agtcaagtcctagcgcactgaccaagactaccgttttgcactgaccaattttttagatctgacca
aaaattttttaagcaatagcaaaaatgttttgtttgcactgaccaacattttttagcactttatt
ctgcaccgaccaatattctttcagatatcaactattttcctattgcaccaaagcatatcaaaat
ttgatacagctttcaaaatatataatgttatttatttgttcttaagttgccgagtatattaata
caactgctattttaaaatactttgccagtttacggttgcttgaacacccaagaaactgaaaaaa
aaattcaattccaggtaaaaatgtattccactcaagcctcctatcctccaaaacctaagtaaat
```

-continued
```
tttcgaagatttagttttctttttttcctggagtttagttgattgtgctccctacactttgttt tctttatattcttaccacttctctaccccttatatccattgagaacccgccgaaacacatcgtt tttattcaattaatgtcattttattggttctcacaccccccaatctgctttcactatattattt tttttgtctagtttccgtatttgaacgttgctactattttatttttcagataacaaaaaagaga gaatcaagttgcaaatcaaaattattttattagaattgttgcgaagaaggatc
``` into a GFP expression vector Tu# 63 as described in Fire et al., Gene 93 (1990), 189.

Transgenic worms were generated as previously described (Mello et al., 1991). The marker rol-6 (plasmid pRF4) and the ncs-1::GFP construct were co-injected into gonads of hermaphrodite animals. Aligning GFP fluorescence images with differential interference Nomarski images allowed the identification of ncs-1::GFP Positive cells (see Table I).

TABLE I

NCS-1 positive cells and their functions

| Positive cells | Function |
| --- | --- |
| Sensory neurons: | |
| AWC (left, right) | Amphid neurons. Chemotaxis to volatile odorants (benzaldehyde, butanone, isoamyl alcohol) |
| ASE (L, R) | Amphid neurons. Chemotaxis to soluble compounds ($Na^+$, $Cl^-$, cAMP, biotin, lysine), egg laying |
| AWB (L, R) | Amphid neurons. Volatile avoidance |
| BAG (L, R) | Sensory neurons |
| PHB (L, R) | Phasmid neurons |
| AWA (L, R) | Amphid neurons. Chemotaxis to volatile odorants (diacetyl, pyrazine, 2,4,5-trimethylthiazol) |
| AFD (L, R) | Amphid neurons. Isothermal tracking behavior. Thermotaxis |
| ADF (L, R) | Amphid neurons. Dauer formation; chemotaxis to soluble compounds (minor) |
| ASG (L, R) | Amphid neurons. Dauer formation (minor); chemotaxis to soluble compounds (minor) |
| PHA (L, R) | Phasmid neurons |
| Inter-neurons: | |
| AVK (L, R) | |
| AIY (L, R) | Isothermal tracking behavior. Thermotaxis |
| Motor-neuron: | |
| RMG | Innervation of muscles in the head |
| Muscle cell: | |
| pm1 | Opening of the metastomal pharyngeal flaps |

Confirmation of GFP staining and NCS-1 positive cells was obtained with antibodies against Ce-NCS-1. Ce-NCS-1 was predominantly expressed in sensory neurons (10 neuronal pairs: AWC, ASE, AWB, BAG, PHB, AWA, AFD, ADF, ASG, PHA). In addition 2 pairs of interneurons (AVK, AIY), 1 motor-neuron (RMG) and 1 muscle cell type (pm1) expressed Ce-NCS-1 (Table I). Most of the NCS-1-expressing neurons were associated with two sensory organs, the head amphids and tail phasmids (FIGS. 1A, 1B). A dendritic, axonal and cell body subcellular distribution was observed with Ce-NCS-1 specific antibodies.

Example 2

Preparation of the ncs-1 Knockout Strain

To investigate the functional role of Ce-NCS-1, knockout (KO) animals were generated. An ncs-1 Tc1 transposon insertion mutant line (ncs-1(pk242::Tc1)) was used to isolate a deletion derivative strain ncs-1(qa401te) (FIG. 2A).

A homozygous mutant ncs-1(pk242) with a Tc1 insertion located at position 5231 relative to the ncs-1 gene fragment was obtained by PCR screening of a Tc1 insertion library, Zwaal et al., Target-selected gene inactivation in *C. elegans* by using a frozen transposon insertion mutant bank. Proc. Natl. Acad. Sci. USA 90 (1993), 7431-7435. Deletion derivatives were obtained as described in (Plasterk, 1995). A strain missing the genomic DNA region between exon 1 and 5 of the ncs-1 gene was isolated (this deletion removed the first initiator ATG). This initial homozygous strain named XA401 ncs-1(qa401te) was back-crossed five times with N2 wild type animals (final name XA406).

The null ncs-1 animals were viable, their developmental timing was normal although they are slightly dumpy, and the NCS-1 protein was no longer present in these KO animals (FIG. 3C). Since 8/10 pairs of NCS-1 positive neurons are known to be involved in chemotaxis and volatile odorant avoidance, several classes of odor responses were measured with the KO strain. Surprisingly, null ncs-1 mutant animals behaved like wild-type worms suggesting that calcium signaling via NCS-1 is not involved in *C. elegans* odorant detection, or that other calcium sensors in olfactory neurons can substitute or compensate for the lack of NCS-1.

Example 3

Thermotaxis Tracking Behavior Assay

As a cold-blooded animal, viable and fertile only within a limited temperature range (~12-26° C.), *C. elegans* has efficient thermosensory behaviors including thermal avoidance for protection against exposure to noxious temperature (Wiftenburg and Baumeister, 1999), and thermotaxis for the perception of physiological (<0.1° C.) changes in local temperature (Mori, 1999). Worms learn to associate a given temperature (the growth temperature) with the presence of food during a conditioning period (acquisition) of several hours (Hedgecock and Russell, 1975). This associative conditioning is reflected by a unique phenotype, the isothermal tracking (IT) behavior, which can be observed on unseeded plates with a radial gradient of temperature with a single animal migrating to the precise growth temperature (+/−0.2° C.) (Hedgecock and Russell, 1975) and then moving isothermally. When the association is disrupted (by food exhaustion), the IT behavior is conserved for several hours (extinction period) then a searching mode is activated and the worms will cross isotherms randomly to seek food at other temperatures (Mori, 1999). But a change in temperature will not lead to a random searching mode, but rather a slow reacquisition of the association between food and the new temperature. As Ce-NCS-1 was found in AFD and AIY, two neurons of the thermotaxis neural circuit, ncs-1(q401te) KO worms were tested for IT behavior at 20° C. (measurement as percentage of worms performing isothermal tracks at 20° C.).

Briefly, 20-30 worms were grown overnight at a constant temperature of 20° C. (the conditioned stimulus) in presence of a fresh lawn of the bacteria strain OP50 (the unconditioned stimulus) on a 6 cm petri dish filled with a medium (NGM) consisting of 1.7% agar, 0.25% bacto peptone, 50 mM NaCl, 25 mM potassium phosphate pH 6.0. Young adults were then transferred on to a fresh plate devoid of bacteria for two minutes. Individual worm were then deposited on a 9 cm Petri dish containing 9 ml of NGM. A radial gradient of temperature was created by placing a vial containing frozen acetic acid on the bottom of the plate and incubating the plate at 26° C. for 90 minutes in presence of a constant humidity of 60%. Upon removal of the animal from the plate, tracks left on the agar surface were photographed.

IT recordings of single worms were visualized after 90 minutes on testing plates as shown in FIG. 3A. Ce-ncs-1 KO animals were abnormal, showing a significant difference in behavior when compared with wild-type (WT) animals (FIG. 3B). 75%+/−8% of WT animals (n=94) exhibited normal IT behavior, whereas only 31%+/−9% of ncs-1 (q401te) mutants (n=96) performed normally. The majority of the KO animals showed irregular IT behaviors, and based on previous descriptions of thermotaxis phenotypes by Mori and Oshima (Mori and Ohshima, 1995), were classified into five categories: 31% were cryophilic, 27% athermotactic, 6% thermophilic, 5% showed intermediate behavior (mixed athermotactic and normal phenotypes), and 31% were normal. The overall IT defects of the ncs-1 mutants (mostly athermotactic and cryophilic) were similar to the phenotypes observed with laser-killed AFD (athermotactic and cryophilic) or AIY (mostly cryophilic) animals, or with ttx-3 (mostly cryophilic) mutants (Hobert et al., 1997), but were clearly different from AIZ (mostly thermophilic) laser-killed animals (Mod and Ohshima, 1995). The thermal avoidance behavior of the ncs-1 knockout strain upon exposure to a noxious temperature was also tested. Noxious temperature causes a withdrawal reflex that differs significantly from thermotaxis behavior, involves different neurons and is influenced by mutations in distinct genes (Wittenburg and Baumeister, 1999). The behavior of the ncs-1(q401te) mutant did not differ from that of wild-type worms in this assay.

To ensure that the diminution of IT behavior with the KO mutant was due to the absence of Ce-NCS-1, a germline rescue of the KO strain was performed using either a 7 kb genomic fragment transgene containing the entire ncs-1 genomic coding region plus ~3 kb of its 5' upstream genomic sequence or a PCR fragment containing the ncs-1 cDNA coding region plus ~3 kb of the 5' upstream genomic sequence (lines RWT, FIGS. 3A, B). Both transgenes were able to rescue the ncs-1 mutant defective phenotype, resulting in restoring IT behavior in 62%+/−9% of animals (n=92, P=0.00001).

Example 4

Calcium-binding is Required for NCS-1 Activity

To test whether the function of Ce-NCS-1 was calcium-dependent, a mutated form of NCS-1 unable to bind calcium (loss-of-function or lf-NCS-1) was generated. 5 μg of purified wild-type NCS-1 or lf NCS-1 were subjected to electrophoresis on 10% SDS-PAGE in the presence of 5 mM $CaCl_2$ or 2 mM EGTA. Proteins were stained for visualization with Coomassie Blue (Geiser et al., 1991).

$^{45}[Ca^{2+}]$-radioactive binding is readily detected with wild-type (wt) NCS-1, but not with the loss-of-function (lf) Ce-NCS-1. A protein control with Red Ponceau staining is shown. 5 μg of recombinant purified wild-type NCS-1 or loss-of-function (lf) NCS-1 were run by electrophoresis on a 10% SDS-PAGE gel, blotted onto nitrocellulose membrane, and incubated with $^{45}[Ca^{2+}]$ followed by several washes, and were visualized by autoradiography for 48 hours (Maruyama et al., 1984). NCS-1nt of the crucial Asp residues of the three EF-hand calcium-binding sites (positions 73, 109, and 157, FIG. 2B) with Ala prevented both $Ca^{2+}$-binding (FIG. 2C) and $Ca^{2+}$-dependent conformational shift of lf-NCS-1 (FIG. 2D). Lines obtained with the lf-ncs-1 transgene (RLF) were assayed for IT behavior (FIG. 3A, B), and showed a defective IT phenotype (27%+/−13%, n=78), despite the expression of the lf-NCS-1 mutated protein (FIG. 3C). This indicates that normal IT behavior is calcium-dependent and requires a functional, calcium-binding NCS-1 sensor.

To determine which cells require NCS-1, a mosaic rescue of the KO animals was performed using AFD (gcy-8 (Yu et al., 1997)) or AIY (ttc-3 (Hobert et al., 1997)) specific promotors driving the expression of ncs-1. A rescued IT behavior (56%+/−5%) was observed with the ttx-3::NCS-1 construct (RAIY animals, n=50, P=0.002), at a level similar to the rescue observed in RWT animals (FIGS. 3A, B). No rescue (12.5%+/−9%) in IT behavior was obtained with the gcy-8::NCS-1 construct (RAFD animals, n=40) (FIGS. 3A, B). These data strongly suggest that for normal IT behavior, NCS-1 function is required in the AIY but not AFD or any other neurons.

Example 5

Increased Level of NCS-1 Affect the IT Behavior of WT Animals

After generating transgenic lines overexpressing NCS-1 (Tg-ncs-1) using the ncs-1 cDNA under the control of the ncs-1 promotor (presence of the construct determined by PCR), the effect in thermotaxis was measured. FIG. 3B shows remarkably that NCS-1 overexpression significantly (P=0.018) increases IT thermotaxis performance (90%+/−10%, n=70) as compared to WT animal behavior (75%+/−8%). These results demonstrate that the level of NCS-1 activity can determine the efficiency of IT performance, and establish that NCS-1 is likely to be essential to the behavior and not merely permissive for IT.

To further characterize Tg-ncs-1 worms, their IT behavior performance was studied in greater details, and compared it with WT worms. The time needed for the acquisition (learning) and the extinction period (memory) of the associative information (presence of food at the temperature of 20° C.) were determined. For acquisition experiments (FIG. 4A), the worms were grown for at least 12 hours in presence of food at 25° C., then were shifted individually for different time intervals onto a seeded plate at 20° C., and their IT behavior at 20° C. was determined. As shown in FIG. 4A, WT worms needed about 68 minutes to reach 50% of their maximal performance level, whereas Tg-ncs-1 worms reached their 50% level after only 24 minutes. Overexpressing NCS-1 worms were therefore 2-3 times faster than the WT to learn the novel conditioning paradigm (food at 20° C.). For both strains, a maximal level of performance was already reached after about 12 hours. For extinction experiments (FIG. 4B), the worms were grown on seeded plates at 20° C. for at least 18 hours, then individual young adult worms were washed at 20° C., transferred onto unseeded plates at 20° C. for different time intervals, and their IT behavior at 20° C. was determined. As shown in FIG. 4B, trained WT worms needed about 3 hours to lose 50% of their maximal performance level, whereas Tg-ncs-1 worms lost 50% of their maximal level only after about 7 hours. Therefore, the extinction period of the associative paradigm (food at 20° C.) was prolonged for at least twice as long with the NCS-1 overexpressing worms as compared to WT worms. For both strains, the return to a baseline level was achieved after about 18 hours. Together, these data indicated that an elevated amount of the NCS-1 calcium sensor protein enhances not only performance, but also learning and memory functions via faster acquisition and longer retention (FIG. 5).

Example 6

Enhancing Long Term Potentiation and Cognition via NCS-1 in Mice 6.1 Experimental Procedures 6.1.1 Production of Transgenic Mice Overexpressing Chick NCS-1:

Thy1-cNCS-1 transgenic mice were generated as follows: a 573 base pairs DNA long fragment encoding the chick NCS-1 (cNCS-1) full-length protein (from the AUG to the stop codon (Nef et al., 1995)) was fused to the adjacent 215 base pairs (SEQ ID NO: 2) corresponding to the 3' untranslated region of cNCS-1 mRNA. The resulting 788 bp cNCS-1 DNA fragment was inserted into a Thy1 promotor cassette. Upon linearization, the 7 kb long Thy1-cNCS-1 construct was microinjected in pronuclei of C57BL/6J-BALB/cJ F1 zygotes using established procedures (Hogan, 1994). Successful transgenesis was determined by PCR analysis of tail genomic DNA obtained from heterozygous siblings using the following oligonucleotide primers: forward 5'-ccacagaatccaagtcgg-3' (SEQ ID NO: 3) corresponded to upstream 5' sequence of the Thy-1 promoter, and reverse 5'-atacgagcccgtcgtagag-3' (SEQ ID NO: 4) was homologous to nucleic acid positions 553-571 of the cNCS-1 coding region.

6.1.2 Tissue Distribution of the cNCS-1 Transgene in the Nervous System:

In situ hybridization (ISH) was performed as previously described (Schaeren-Wiemers and Gerfin-Moser, 1993). Briefly, antisense dig-labelled RNA probes (riboprobes) were synthesized as indicated by the manufacturers manual (DIG-RNA labelling kit, Roche Biochemicals) using specific 3'UTR sequences (nucleic acid positions 636-750 and 501-750) of chick NCS-1 as a template to avoid any cross-hybridization with the endogenous mouse ncs-1 mRNA transcripts. Brains from transgenic and WT animals were dissected, embedded in Tissue Tek, immediately frozen in isopentan with dry ice. Tissues were kept at 80° C. until processing. 12 μm thick sections were prepared at −15° C. with a microtome, mounted on SuperFrost Plus slides (Menzel-Gläser), dried for 20 minutes at RT, and either conserved at −20° C. or directly used for ISH. Following post-fixation in 4% paraformaldehyde and PBS, the sections were incubated 2× for 15 min in PBS containing 0.1% active DEPC, then equilibrated for 15 min in 5×SSC. Sections were prehybridized in hybridization mix (50% formamide, 5×SSC, 5× Denhardt's solution, 0.25 mg/ml yeast tRNA, 0.5 mg/ml salmon sperm DNA) for 2 hours at 65° C. After addition of heat denatured riboprobes at 500 ng/ml, hybridization was performed o/n at 65° C. Sections were then washed at room temperature for 30 min in 2×SSC, at 72° C. for 1 hr in 2×SSC, at 72° C. for 30 min in 0.1×SSC, and finally equilibrated in Buffer 1 (Maleic acid 0.1M, NaCl 0.15M, pH 7.5). Sections were then incubated for 2 hr with alkaline phosphatase coupled anti-digoxigenin antibodies (Roche Biochemicals) at a dilution of 1:3000 in Buffer 1 containing 0.5% Blocking reagent (Roche Biochemicals). The excess of antibody was removed by 2× washes for 15 min in Buffer 1, and then the sections were equilibrated in Buffer 2 (TrisHCl 0.1M, NaCl 0.1M, $MgCl_2$ 50 mM, pH 9.5). Color development was done at room temperature in the dark with Buffer 2 containing NBT/BCIP (Gibco) and levamisole (0.24 mg/ml final concentration), and the staining was stopped by adding Tris 10 mM, and EDTA 0.1 mM at pH 8. The sections were then briefly rinsed in bi-distilled water and mounted with VectaMount (Vector Laboratories). Detailed morphological analysis of the total number of synapses, the shape and morphology of end plates, as well as the amount of nerve sprouting was performed as described elsewhere (Caroni et al., 1997).

6.1.3 NCS-1 Level of Overexpression:

Total protein extracts from brain tissue of transgenic and WT animals were produced as follow: dissected hippocampus were homogenized in PBS buffer containing protease inhibitors (tablets EDTA free, Roche Biochemicals) and sonicated 3× for 5 sec (at 10 Watts) on ice using a Vibracell sonicator (Sonics&Materials inc.). The homogenate was cleared by centrifugation at 4° C. for 30 min at 12'000 g. The protein concentration of the lysate was determined by the Bradford protein assay (Bio-Rad, Hercules, Calif.) using BSA as a standard. 30 μg of total protein was resolved by SDS-PAGE using standard methods. The proteins were then transferred to PVDF membranes by electroblotting according to the manufacturer directives (Novex), and processed for immunodetection. PVDF membranes were incubated at room temperature for 30 min in Blocking buffer (PBS containing 5% non-fat milk and 0.05% Tween 20), then at room temperature for 2 hr with a specific anti-human NCS-1 polyclonal antibody diluted 1:500 in Blocking buffer. The immune complex was revealed by chemiluminescence as described earlier (ECL system, Amersham). Staining of the α subunit of calmodulin-dependent kinase II with a monoclonal anti-rat antibody (Calbiochem) diluted 1:2000 was used as an internal reference control for insuring that similar amount of protein was loaded, transferred, and detected. After exposure, the film was scanned on an Imaging Densitometer (Bio-Rad) and NCS-1 signals were quantified (Molecular Analyst software, Bio-Rad).

6.1.4 Hippocampal Slice Electrophysiology:

Recordings were carried out as previously described (Muller et al., 1996). Briefly, hippocampal slices were prepared from young adult (2-4 months old) transgenic (Tg26 and Tg 200) mice and their wild type littermates (WT) by decapitation and slicing using a tissue chopper. They were maintained in an interface chamber under continuous perfusion with a medium containing (in mM): NaCl 124, KCl 1.6, $CaCl_2$ 2.5, $MgCl_2$ 1.5, $NaHCO_3$ 24, $KH_2PO_4$ 1.2, glucose 10 and ascorbic acid 2; pH 7.4, temperature 33° C. Excitatory postsynaptic potential (EPSPs) were elicited with stimulation electrodes made of twisted nichrome wires placed in the Schaffer collateral pathway and recorded in the dendritic area (*stratum radiatum*) of the CA1 region. LTP was induced using theta burst-patterned stimulation (five bursts at 5 Hz, each composed of 4 pulses at 100 Hz) repeated twice consecutively at 10 s interval. The EPSP slope was monitored continuously and the results expressed as the ratio of the changes observed 30 min and 60 min after stimulation versus baseline values. To analyze the NMDA component of burst responses, trains of 4 pulses at 100 Hz were elicited repetitively (0.03 Hz) using a priming paradigm to suppress inhibitory responses. This was done by using a second stimulation electrode and evoking a synaptic response on a separate, independent input 200 ms prior to the burst response. The NMDA component was then determined as the difference between the burst responses recorded before and after application of 50 µM D-AP5. Facilitation was measured as the ratio of slopes of EPSPs evoked at short intervals (25-500 ms) using a paired-pulse paradigm.

6.1.5 Synaptic Fatigue at the Neuromuscular Junction:

Experiments were carried out with the left hemidiaphragm incubated in a solution containing 40% Leibovitz L-15 medium with the following ion concentrations ($Na^+$ 1 mM, $K^+$ 1 mM, $Ca^{2+}$ 2.5 mM, $Mg^{2+}$ 1 mM) at pH 7.5 with HEPES. The phrenic nerve was stimulated via a suction electrode, and intracellular recordings of endplate potentials (EPPs) were performed. Membrane potentials were between −65 and −75 mV. Nerve stimulation was a train of 13 pulses delivered at 100 Hz, once every 6 sec. Muscle fiber contraction were blocked by the addition of 1-1.5 µg/ml d-tubocurarine. At these concentrations, EPPs were between 1-3 mV in amplitude. Responses to 15 to 30 consecutive stimulus trains were averaged for each endplate, and each averaged EPP amplitude in a train was expressed relative to the amplitude of the first average EPP of the same train. To avoid interference by non-linear summation (Martin, 1976), data collection in an experiment was discontinued when the membrane potential had declined by more than 5 mV.

6.1.6 Behavioral Studies:

Neurological tests: Groups of Tg26, Tg200 and their WT littermates (n=12 per group) were used to evaluate neurological functions as previously described (Higgins et al., 2001). Locomotor activity was measured in unfamiliar photocell cages (36×24×19 cm, Benwick Electronics, UK), and both horizontal and vertical activity was recorded over a 60 min period.

Morris Water Maze: One group of Tg26 and their WT littermates (n=10 per group) were trained to find a fixed submerged a platform (8 cm diameter, 1 cm below surface) within a circular pool (diameter, 1 m; height, 30 cm) filled with milky water (depth 20 cm; 21±1° C.). Platform location was balanced within groups. External visual cues were placed around the pool to facilitate navigation of the animals. Each mouse received 1 training session per day over 5 consecutive days (three trials per session) in which they were placed facing the wall of the pool and allowed to locate the hidden platform. The time the mouse needed to locate the target (escape latency) and the swim path and swim speed were measured using an automated video motility system (HVS Image, Hampton, UK). A maximum trial length was 60 sec. Assessment of spatial learning was conducted in probe trials performed 1 hour after session 3 and 5. In the second experiment, the probe test was also performed 5 days following the last training session. Escape latency data were analyzed with two-way ANOVA with genotype as independent factor and training sessions as repeated measures. The probe test data were analyzed with a one-way ANOVA. Posthoc comparisons were carried out using Newmann Keuls test.

Active avoidance and shock threshold tests: Tg26 and their WT littermates (n=12 per group) were tested. The active avoidance test was performed in four identical two-chamber boxes (Gemini II avoidance system, San Diego Instruments, USA). Each box was equipped with a wire grid floor, stimulus light located on the ceiling of each compartment, and an automatic sliding door separating the two chamber which was kept open during the training. Animals received 20 trials per day (trial block) run over 10 consecutive days. Each training session started with 5 min acclimation phase and animals were trained to avoid a 0.2 mA stimulus by responding to a visual cue light located in each chamber. A 20 s Intertrial interval (ITI) was used. If the mouse did not cross within 10 s of the cue presentation, a shock (0.2mA) was delivered either until the animal crossed to the alternate side (escape response) or after 10 s had elapsed. Shock threshold was determined for Tg26 and WT (n=6 per group). Each mouse was tested in operant chamber (14 cm×14 cm×13 cm; Med Associates, VT) with a wire grid floor and given manually 1 s foot shocks. Shock levels began at 0.05 mA, and increased in 0.05 mA steps with 30 s interval between shocks, until both flinch (any detectable response) and vocalization had been induced. Active avoidance data analysis was conducted by two-way ANOVA with genotype as independent factor and training sessions as repeated measures. Posthoc comparisons were carried out using Newmann Keuls test.

Light/dark exploration and startle tests: Ten Tg26 and ten WT mice were tested in the light-dark test as described previously (Kew et al., 2000). The time spent in each compartment, the number of attempts to enter the lit compartment and the number of transitions from the dark to the lit compartment were recorded during the 5 min test period. Differences between lines were compared with Student's t-test. Startle testing was conducted in startle devices (SR-LAB, San Diego Instruments, USA) as described previously (Kew et al., 2000). Each session was initiated by a 5 min acclimation period followed by five successive 110-dB trials. These trials were not included in the analysis. Ten different trial types were then presented: startle pulse alone (ST 110, 110-dB/40 ms); six different prepulse trials in which either 20-ms-long 74, 82, or 90-dB stimuli were presented alone (P74, P82 and P90) or preceded the 110-dB pulse by 100 ms (PP74, PP82 and PP90); and finally one trial in which only the background noise was presented to measure baseline movement in the cylinders. All trials were presented in pseudorandom order, and the average intertrial interval was 15 s. Analysis of the data was carried out with a two-way ANOVA with genotype as independent factor and the stimuli as the repeated measure.

6.2 Generation and Selection of Transgenic Mice Overexpressing NCS-1:

Several transgenic (Tg) mouse lines were constructed using the full-length coding sequence of the chick neuronal calcium sensor-1 (cNCS-1) and a small region of its 3'-untranslated region placed under the control of the Thy1 promoter. This promoter drives neuron-specific transcription of the transgene starting only in postnatal stages P6-10 (Caroni, 1997; Kelley et al., 1994), therefore strongly reducing the potential problems associated with the overxpression of a transgene during embryonic neuro-development. The specific expression of the thy1::cNCS-1 gene construct was determined by in situ hybridizations (ISH) of serial brain and spinal chord sections derived from adult Tg mice. To differentiate from the endogenous mouse ncs-1 transcripts, the 3'-untranslated region of the chick NCS-1 cDNA was used as antisense probes (FIG. 7A). Based on cNCS-1 transcript distributions and expression levels in the brain, two independent transgenic lines, named Tg26 and Tg200, were selected. The overall and specific brain distributions of cNCS-1 positive signals for both Tg lines are described in FIG. 7 and Table II.

The overexpression of cNCS-1 in Tg26 was only observed in two main regions: 1) the hippocampus, with the pyramidal cell layers of the CA1-2-3-4 region and the granule cell layer of the dentate gyrus, and 2) the spinal chord, with the motor neurons and few sensory nuclei in the medulla (FIG. 7A, Table II). Weak but detectable labeling in Tg26 was also observed in the superior colliculus and the deep cerebellar nuclei. With Tg200, however, cNCS-1 overexpression was significantly higher in the hippocampus and motor neurons, and was observed in several additional brain regions. Indeed, moderate to strong cNCS-1 labeling was observed in the neocortex, the pons, parts of the limbic cortex, in the olfactory, auditory and visual systems, the thalamus and hypothalamus as well as the cerebellum (see FIG. 7A and Table II). cNCS-1 signals in the hippocampus were clearly stronger in Tg200 than in Tg26 (FIGS. 7B, 7C and 7D), and not surprisingly, corresponded to higher amount of total NCS-1 protein in the hippocampus (FIG. 7F). A scan analysis of the Western blot intensity indicated that, when compared to the WT endogenous level, the amount of NCS-1 was two fold higher in Tg26, and six fold higher in Tg200. NCS-1 overexpression was also higher in motor neurons of Tg200 when compared to Tg26 (FIG. 7E). Overall, the thy1::cNCS-1 expression was stronger and broader in glutamatergic and cholinergic structures than in monoaminergic structures. For both Tg26 and Tg200 lines, no cNCS-1 overexpression could be detected in the white matter.

cNCS-1 Tg animals appeared normal and healthy, their life span was comparable to WT littermates, and had no gross apparent locomotor or neurological differences. Light microscopy and histological analyses of Tg26 and Tg200 revealed no major anatomical or cellular differences in the nervous system, and the architecture of the hippocampus and of the spinal chord were normal. A detailed analysis of changes occurring at the NMJ of Tg26 and Tg200 during post-natal development indicated that the total number of synapses, the shape and morphology of end plates, as well as the amount of nerve sprouting were similar to WT littermates.

6.3 Enhancement of Hippocampal Long Term Potentiation in Tg26 and Tg200

Upon theta-burst patterned stimulation of the Schaffer collaterals, CA1 pyramidal neurons in slices prepared from the hippocampus undergo a phenomenon called long term potentiation (LTP). To investigate the potential role of NCS-1 overexpression in synaptic facilitation, LTP levels in Tg26, Tg200, and WT littermates were measured and compared. Slices overexpressing NCS-1 had a significantly larger LTP (FIG. 8A). As measured 30 minutes after the initial stimulus, the LTP enhancement was superior in Tg200 as compared to Tg26, and was significantly larger in Tg26 as compared to WT. These observations could directly be correlated to the relative amount of NCS-1 present in the hippocampus (FIG. 8B). These data strongly suggested that the observed enhancement of LTP in CA1 neurons was NCS-1 dose-dependent, with the highest amount of NCS-1 resulting in a larger LTP. Furthermore, the statistically significant enhancement of LTP was present from the onset of LTP and lasted for as long as 70 min after the initial stimulation, suggesting that the effect of NCS-1 overexpression occurred already during the early phases of LTP.

Since the induction of LTP is known to be critically dependent upon NMDA receptor activation (Bliss and Collingridge, 1993; Nicoll and Malenka, 1995) it was tested whether or not the LTP enhancement by NCS-1 was mediated via an up-regulation of NMDAR-dependent excitatory post-synaptic responses (EPSPs). When burst responses used to induce LTP in the presence or absence of the NMDA receptor antagonist D-AP5 were analyzed, significant difference on EPSPs could be observed between Tg200 and WT littermates. The summation of responses within the bursts was much larger in Tg200 than in WT (FIG. 9A). The difference was particularly important when comparing the last bursts in the series of 5 used to induce LTP. As a result of this, the size of the NMDA component of these burst responses was also proportionately enhanced in Tg200 (FIG. 9B), indicating that the NCS-1 effect on LTP was probably mediated through a more efficient activation of NMDAR receptors during burst stimulation (FIGS. 9A and 9B). This observation clearly suggested a presynaptic modulation of facilitation by NCS-1. As illustrated in FIG. 10, paired-pulse facilitation was indeed found to be enhanced in a NCS-1 dose-dependent manner, Tg200 being better than Tg26, itself better than WT (FIGS. 10A and 10B). The observed differences were statistically significant. The facilitation increase was observed at all tested time intervals and was not associated with a change in the time course of facilitation (FIG. 10B). The latter result strongly suggested a presynaptic role for NCS-1. Taken together, these data suggested that the enhancement of hippocampal LTP in area CA1 and of the paired-pulse facilitation between CA3 and CA1 neurons were dependent on the amount of pre-synaptic NCS-1.

Similarly, a higher amount of NCS-1 in motor neurons could also contribute to an increase of neurotransmitter release at NMJ. To test this hypothesis, end plate potential (EPP) amplitude analyses were performed with Tg200, the line with the highest level of NCS-1 at NMJ. At normal physiological conditions, a train of stimuli applied to a motor nerve will evoke a depression of EPP amplitudes during the train, a phenomena called synaptic fatigue caused by the depletion in the pool of vesicles ready to be fused to the synaptic membrane for neurotransmitter release. In response to identical stimulus trains, Tg200 showed, after normalization, a more severe depression than WT controls using the diaphragm NMJ preparation (FIGS. 11A and 11B). These data indicated that NCS-1 overexpression was enhancing presynaptic neurotransmitter release and causing a rapid depletion of the pool of synaptic vesicles ready to be secreted at NMJ. The same phenomenon of neurotransmitter vesicle depletion occurs when the calcium concentration in the extracellular bath is increased. These finding suggested that the presynaptic overexpression of NCS-1 had a similar effect than increasing the extracellular calcium ion concentration, and subsequently, than increasing intracellular calcium signaling.

6.4 Enhancement of Learning and Memory Behaviors with Tg26

The electrophysiological studies indicated that NCS-1 was facilitating LTP in the hippocampus, a form of synaptic plasticity that plays a major role in learning and memory processes. Therefore Tg26, Tg200, and WT littermates were investigated for neurological and cognitive functions. Initial examinations revealed no overt neurological phenotype, and mice from both Tg26 and Tg200 lines showed good general health and normal body weight growth when compared to WT. No differences in motor coordination, swim ability, balance and muscular functions were detected, and furthermore, no significant differences were noted between the three groups in terms of general open field activity.

In a preliminary water maze experiment using a relatively massed trials protocol, (i.e. 3 trials/block, 2 blocks/day), both WT controls and the Tg26 line showed equivalent cued and spatial learning, although Tg200 line demonstrated a mild impairment in spatial learning as revealed by a probe test conducted immediately post training. Importantly, cued learning and swim speeds were similar between the groups. Therefore it was decided to focus on the Tg26 line, in which NCS-1 overexpression was more restricted to the hippocampus, speculating that the wider and quantitatively greater expression of NCS-1 in Tg200 may be detrimental to cognitive performance. Using a spaced trial water maze protocol in experimentally naïve mice, (i.e. 2 trials/block, 1 block/day, 5 days) both WT and Tg26 mice showed similar rate of acquisition (FIG. 12A). However, a probe test conducted 1 h after the $5^{th}$ trial block revealed improved spatial preference for the island location in the transgenic line Tg26 (FIG. 12B). A further 5 trial block was conducted (Week 3; FIG. 12C), and, on this occasion, the Tg26 line was significantly faster than WT controls in terms of latency to locate the island platform. Probe tests conducted after blocks 3 and 5 during this phase were consistent with improved learning in the Tg26 mice (FIG. 12D). A final probe test was conducted 5 days after the second phase (Week 3) and again indicated improved performance in the Tg26 mice compared to WT (FIG. 12E). At this time point, Tg26 mice, but not the WT controls, still demonstrated a significant preference for the island quadrant, thus revealing better retention abilities for Tg26 animals.

To further investigate differences in learning ability between Tg26 and WT mice, a conditioned active avoidance test was conducted. Another group of experimentally naïve mice was tested for avoidance to a scrambled foot shock signaled by a visual conditioned stimulus. Again, Tg26 mice showed improved learning performances during the training as compared to the WT mice (FIG. 13A). The greatest differences between the two lines were detected at the $3^{rd}$ and $4^{th}$ trial block. By the $5^{th}$ session, Tg26 mice reached nearly a maximal level of performance, while WT mice reached a similar level of performance by the $8^{th}$ trial block. Tg26 mice also displayed significantly lower avoidance latencies compared to the WT mice (FIG. 13B). In contrast, no differences in the escape latencies were detected between Tg26 and WT mice, consistent with both groups displaying similar responses to the electrical shock. To further assess possible differences in pain perception between the two lines, shock threshold analysis was conducted at the end of the active avoidance test. The shock levels at which Tg26 and WT mice first detected the shock (flinch) or emitted vocalizations were similar (flinch: WT=0.15±0.0 mA and Tg26=0.14±0.1 mA; vocalizations: WT=0.42±0.0 mA and Tg26=0.40±0.1 mA). This suggests that the improved learning ability of Tg26 mice is not a consequence of changes in pain perception caused by overexpression of NCS-1.

Because differences in anxiety or stress-reactivity might underlie differences in learning performance between Tg26 and WT mice, responses to aversive stimuli were also determined and compared. First the innate avoidance behavior of the Tg26 and WT mice was studied for a bright environment using the light-dark test. No differences in anxiety measures were detected between the two lines. The amount of time spent in the lit compartment and the numbers of transitions between the light and dark compartment were comparable for the two lines. The defensive reactions of the animals were also compared to various acoustic stimuli (74, 82, 90 and 110 dB). Again, Tg26 and WT mice displayed a similar startle reflex threshold. In the same procedure we investigated whether or not NCS-1 overexpression influenced prepulse inhibition (PPI) of acoustic startle, which is also dependant on hippocampal function. PPI is the modulation of the startle response by a weak prepulse, and is considered as an index of sensorimotor gating which is the process by which inhibitory pathways filter multiple stimuli and allow attention to be focused on one stimulus. No differences were detected in the levels of PPI between Tg26 mice and their WT littermates at any of the prepulse intensities tested, 74, 82 and 90-dB.

6.5 Summary

In the above described experiments two transgenic mouse lines were tested, Tg200 and Tg26, overexpressing the vertebrate neuronal calcium sensor-1 to study synaptic plasticity and associative learning and memory. Line Tg26 was selected because the level of NCS-1 overexpression is mild and is mostly restricted to the hippocampus, whereas Tg200 was selected because the NCS-1 overexpression reached a much higher level and had a broader distribution. Interestingly, Tg26 showed an enhancement of LTP, and improved spatial learning using the Morris water maze and active avoidance tests when compared to WT. The Tg26 animals demonstrate faster acquisition of active avoidance learning compared to WT littermate controls. At the cellular level, the overexpression of NCS-1 resulted in dose-dependent increase of LTP in the CA1 region of the hippocampus. It is tempting to relate the improved learning abilities of Tg26 mice to the long lasting increase in the synaptic efficacy revealed in the hippocampus. Although the increase of LTP was only determined in CA1 region of the hippocampus, it is most likely that NCS-1-dependent LTP facilitation might also occur in the dentate gyrus, and in other CA neurons of the hippocampus where NCS-1 was overexpressed. The present findings extend previous studies describing smart mice that have modified level of expression of key synaptic components important for the induction or maintenance of long-term potentiation such as NMDA receptor subunit NR2B (Tang et al., 1999), tissue-type plasminogen activator (tPA) (Madani et al., 1999), growth associated protein GAP-43 (Routtenberg et al., 2000), calcineurin (Malleret et al., 2001), where an increase of LTP was correlated to enhanced performances in spatial learning tasks. Furthermore, data obtained in accordance with the present invention supports many other observations where mice with a genetic disruption or alteration of crucial synaptic elements like αCaMKII, CREB or NR1, resulted in lower or no LTP together with impaired learning and memory skills (Giese et al., 1998; Mayford et al., 1996; Silva et al., 1992; Silva et al., 1992) (Bourtchuladze et al., 1995) (Tsien et al., 1996; Tsien et al., 1996). However, data obtained with other genetically targeted mice have questioned the link between hippocampal LTP and performances in spatial learning tasks. Indeed, knock-outs of AMPA receptor GluR1, GluR2, PSD-95, OFQ or PTPdelta have been described in which altered expression of LTP had not been matched by lower performance in hippocampal-dependent learning (Jia et al., 1996) (Zamanillo et al., 1999) (Migaud et al., 1999) (Koster et al., 1999; Uetani et al., 2000; Wei and Xie, 1999) (reviewed in (Picciotto and Wickman, 1998)). For instance, in Tg200 mice that show stronger and wider overexpression of NCS-1 in the brain, the increase of CA1 LTP did not correlate with an improved spatial learning performance which depend on complex functional interactions (competition and synergism) between the hippocampus and other brain structures (for review see (Kim and Baxter, 2001; Rossi-Arnaud and Ammassari-Teule, 1998)). It is therefore possible that the limited learning performances of Tg200 line could be related to the overexpression of NCS-1 in other corticolimbic structures known to exert an inhibitory control on spatial information processing.

Interestingly, the magnitude of LTP facilitation was correlated to the amount of NCS-1 present in the hippocampus. This NCS-1-dependent increase in LTP could be most likely mediated through a presynaptic mechanism (FIG. 14). Similar observations were obtained with C. elegans in Examples 3 to 5. A presynaptic effect of NCS-1 was also reported at the NMJ of flies and frog (Olafsson et al., 1995; Rivosecchi et al., 1994). At NMJ, however, synaptic depression is caused by a progressive decrease in the mean number of transmitter quanta release by action potentials. Either the depletion in the pool of releasable vesicles (Mallart and Martin, 1968), or the modulation of release from the presynaptic terminal by adenosine (Redman and Silinsky, 1994) has been proposed to mediate synaptic depression at NMJ. The present data are thus consistent with the idea that, in the presynaptic nerve terminals of motor neurons overexpressing NCS-1, $Ca^{2+}$ influx/signaling is increased, or sequestering of $Ca^{2+}$ is impaired as compared to WT. The increased number of transmitter quanta release during initial action potentials is technically difficult to determine at vertebrate NMJ, but is likely to induce subsequent synaptic fatigue and diminished responses. NCS-1 enhanced calcium signaling mechanisms could also be at play during LTP in hippocampal slices of NCS-1 transgenic animals, as shown here. Furthermore, the present data suggest a presynaptic role for NCS-1, but do not exclude a postsynaptic effect since NCS-1 is clearly present on both sites of many synapses (Martone et al., 1999). In the absence of proven in vivo NCS-1-dependent molecular or cellular pathways, the proposed mechanisms still represent a working hypothesis. NO synthase, PDE, calcineurin are among the targets known to be regulated by NCS-1 in vitro (Schaad et al., 1996). NCS-1 has also been shown to interact with a phosphatidylinositol 4-OH kinase (Zhao et al., 2001), and to substitute for CaM-dependent potassium channels in vivo (Schaad et al., 1996). All these therefore represent potential targets responsible for mediating the NCS-1 effect observed in vivo. Furthermore, a very recent study has implicated NCS-1 in the regulation of P/Q type $Ca^{2+}$ calcium channels through Src-family tyrosine kinase in cultured cells (Weiss and Burgoyne, 2001). Despite synaptic fatigue revealed by electrophysiology recording at the NMJ it was found that both transgenic lines had normal general motor performances as determined using muscular strength, locomotor activity or swim abilities. The neurophysiological changes produced by NCS-1 overexpression seems therefore too subtle to be detected at behavioral level. It should be also stressed that in Tg26 mice the overexpression of NCS-1 had no effect on emotional behaviors. These mice displayed a normal defensive reactions to acoustic stimuli and normal neophobic responses in the light-dark test. This implies that the improved learning ability of Tg26 mice is not a consequence of changes in stress reactivity caused by overexpression of NCS-1 in the hippocampus. This is an important observation given the central role of the hippocampus in the modulation of stress and anxiety-related behaviors (Gray, 1982). It seems therefore that in the hippocampus NCS-1 may be an essential component of the neural circuitry subserving learning and memory processes. In line with this hypothesis, it was recently shown that the induction of NCS-1 mRNA is part of the transcriptional response associated with activity-dependent neuronal plasticity in vivo (Genin et al., 2001). Taken together the present findings would suggest that the overexpression of NCS-1 in the hippocampus may facilitate learning and memory processes by affecting many important neuronal functions including neurotransmitter release, intracellular signaling, synaptic plasticity and gene expression cascade required for formation of new memories.

Example 7

NCS-1 Knock-out Mice 7.1 Experimental Procedures 7.1.1 Production of NCS-1 Knock-out Mice Exon 1 of the mouse NCS-1 gene was disrupted by replacing it with a LacZ reporter gene cassette. The targeting construct used is shown in FIG. 15A. FIG. 15B shows the targeting of exon 1 as well as the localization of the probes used for the determination of successful homologous recombination by Southern blot. In FIG. 15C, the PCR positive control construct is depicted. FIG. 15D shows again the targeting with the localization of the primers NeoI and Ctl5 for the PCR analysis of successful homologous recombination.

7.1.2 Behavioral Studies

Knock-out mice are tested for behavioral defects in tests including Morris water maze, fear conditioning, active and passive avoidance as described below. Moreover, their general levels of, for example, locomotor activity, cognition, memory, learning, fear, anxiety are assessed. Mice are weighed weekly and general appearance checked. All mice are individually housed.

Neurological Tests

Locomotor activity: The mice are placed into a novel test chamber for a 1 h period which consists of a Plexiglas® box (20 cm×20 cm×27 cm) with sawdust bedding on the floor. The animal's movement is recorded using an electronic monitoring system (Omnitech Electronics Inc., Columbus, Ohio, USA). Movement of the animal results in interruption of an array of photobeams from vertically and horizontally located infrared sources placed around the test chamber. Total distance travelled (cm) and number of rears are measured.

Wire manouvre: Mice are placed by forepaws on an elevated wire rod and the latency to fall is noted. Cut-off time is 60 s and the best score from 3 attempts is recorded.

Grip strength: Mice are forced to pull on a strain gauge and the release point is recorded. The best score from 5 attempts is recorded.

1 meter swim test: Mice are placed in a straight swim tank (1 m long×6 cm wide). Latency to swim the distance and climb onto the platform is noted. Mice are given 3 trials over 3 consecutive days and the fastest time is recorded.

Rotarod: Mice are placed on a constant speed rotarod and the latency to fall is noted. Cut-off time is 120 s and the best score from 3 trials is taken. 2 speeds are used: 16 rev/min, 32 rev/min.

In addition, body temperature, coat appearance, secretory signs, body posture are also noted.

Y-maze

Mice are placed in a Y-maze made of black perpex (each arm is 53 cm long, 15 cm wide and 30 cm in height) for 5 min. A camera is positioned above the maze and the experimenter observes the animals on a monitor in an adjoining room. The number of arm entries and their entry sequence is noted to calculate an alternation measure.

Morris Water Maze

The water maze consists of a grey circular tank (1 m diameter) filled with water made opaque by the addition of a latex solution (E-308; Induchem, Voletswil, Switzerland). Pool temperature is maintained at 21+1° C. For the hidden platform task, the escape platform (8 cm diameter) is positioned 1 cm below water level in the centre of one of the pool quadrants. For the cued task, platform position is signalled by the addition of a small black flag which is positioned in the centre of the submerged platform. The walls surrounding the water maze are hung with posters and flags which serve as visual cues and are visible during all stages of training and testing. Movement of the mice within the pool is tracked and analysed with a computer based video tracking system (HVS Image, Hampton, UK).

For cued training, mice are placed in the pool facing the edge at one of four start positions (NE, SE, SW, NW), and are required to locate the flagged platform whose position varies across trials. Each mouse receives a total of 12 trials (three trials per block, 2 blocks per day, 2 day duration). Intertrial intervals average 10 min, and maximum trial length is 60 s. If mice fail to find the platform within 60 s, they are guided to its position by the experimenter. All mice are allowed to remain on the platform for a 10 s period before being removed and returned to the homecage. The cued task is followed by the place task, in which mice are required to locate a submerged hidden platform whose position remains fixed throughout training. Platform location is balanced within groups. Each mouse receives 8 blocks of training trials over four consecutive days (three trials per block, timing as per cued test) in which they are placed in the pool at one of four start positions, and allowed to locate the hidden platform. Assessment of spatial learning is conducted in probe trials performed both 30 min after block 4, and 24 h following the final trial. In each probe trial the platform is removed from the pool, and the path swam by each mouse recorded over a 60 s period.

Active Avoidance

Mice are placed into a 2-compartment chamber within which they can freely pass between compartments (San Diego Instruments, USA). Each trial begins with the side currently occupied by the mouse being illuminated by a 10 s light (CS), which is used to signal a footshock (0.2 mA) of maximum duration 20 s. (NB. the mice never receive this shock duration for they either escape within 1 s to the other (unshocked) compartment, or learn to avoid the shock altogether). This is followed by a variable timeout period (mean 20 s, range 15-25 s) (no light) in which the mouse can freely explore the chamber. Following the timeout, the next trial begins. Shock can be avoided either by a shuttle to the next compartment during the CS period, (i.e avoidance) or escape at any time during the shock presentation. Ten daily test sessions are run with each session consisting of 20 trials. The dependent measure is % avoidance.

7.2 Summary

Since the NCS-1 overexpression increases long term potentiation (LTP) and improves cognitive phenotypes with better learning and memory capabilities (based on electrophysiological and behavioral analyses), it is expected that a mouse line lacking NCS-1 gene expression (ncs-1 knock-out mice) have the reverse phenotype including less memory and learning, and lower or changed levels of LTP.

18 chimeric mice with 10 to 95% chimerism were obtained. These mice were crossed to obtain heterozygous founders. In these mice, exon 1 of the endogenous ncs-1 gene is disrupted and is therefor no longer functional. This will cause the absence of the NCS-1 protein in the brain. These mice are tested for behavior defects (i.e. Morris water maze, fear conditioning, active and passive avoidance) and assessed for their general levels of locomotor activity, cognition, memory, learning, fear, anxiety, which is compared to the level of wild type mice and transgenic NCS-1 mice. Their level of LTP/LTD in the hippocampus and other brain regions is determined and compared with wild type and transgenic NCS-1 animals. Moreover, NCS-1 knock-out mice are used to explore the role of NCS-1 in development and synaptogenesis, and to determine its biochemical function e.g. the confirmation and characterization of its binding partners

REFERENCES

Bartlett, S. E., Reynolds, A. J., Weible, M., Jeromin, A., Roder, J., and Hendry., I. A. (2000). PtdIns 4-kinasebeta and neuronal calcium sensor-1 co-localize but may not directly associate in mammalian neurons. J Neurosci Res 62, 216-24.

Bliss, T. V., and Collingridge, G. L. (1993). A synaptic model of memory: long-term potentiation in the hippocampus. Nature 361, 31-9.

Bourne, Y., Dannenberg, J., Pollmann, V., Marchot, P., and Pongs, O. (2001). Immunocytochemical localization and crystal structure of human frequenin (neuronal calcium sensor 1). J Biol Chem 276, 11949-55.

Bourtchuladze, R., Frenguelli, B., Blendy, J., Cioffi, D., Schutz, G., and Silva, A. J. (1995). Deficient long-term memory in mice with a targeted mutation of the cAMP-responsive element-binding protein. Cell 83, 979-92.

Braunewell, K., Riederer, P., Spilker, C., Gundelfinger, E. D., Bogerts, B., and Bernstein, H. G. (2001). Abnormal localization of two neuronal calcium sensor proteins, visinin-like proteins (vilips)-1 and -3, in neocortical brain areas of Alzheimer disease patients. Dement Geriatr Cogn Disord 12, 110-6.

Braunewell, K. H., and Gundelfinger, E. D. (1999). Intracellular neuronal calcium sensor proteins: a family of EF-hand calcium-binding proteins in search of a function. Cell Tissue Res 295, 1-12.

Burgoyne, R. D., and Weiss, J. L. (2001). The neuronal calcium sensor family of Ca2+-binding proteins. Biochem J 353, 1-12.

Caroni, P. (1997). Overexpression of growth-associated proteins in the neurons of adult transgenic mice. J Cell Biol 136, 679-92.

Caroni, P., Aigner, L., and Schneider, C. (1997). Intrinsic neuronal determinants locally regulate extrasynaptic and synaptic growth at the adult neuromuscular junction. J Cell Biol 136, 679-92.

Cox, J. A., Durussel, I., Comte, M., Nef, S., Nef, P., Lenz, S. E., and Gundelfinger, E. D. (1994). Cation binding and conformational changes in VILIP and NCS-1, two neuron-specific calcium-binding proteins. J Biol Chem 269, 32807-13.

De Castro, E., Nef, S., Fiumelli, H., Lenz, S. E., Kawamura, S., and Nef, P. (1995). Regulation of rhodopsin phosphorylation by a family of neuronal calcium sensors. Biochem Biophys Res Commun 216, 133-40.

Fontana, G., and Blaustein, M. P. (1993). Calcium buffering and free Ca2+ in rat brain synaptosomes. J Neurochem 60, 843-50.

Geiser, J. R., van Tuinen, D., Brockerhoff, S. E., Neff, M. M., and Davis, T. N. (1991). Can calmodulin function without binding calcium? Cell 65, 949-59.

Genin, A., Davis, S., Meziane, H., Doyere, V., Jeromin, A., Roder, J., Mallet, J., and Laroche, S. (2001). Regulated expression of the neuronal calcium sensor-1 gene during long-term potentiation in the dentate gyrus in vivo. Neuroscience 106, 571-7.

Giese, K. P., Fedorov, N. B., Filipkowski, R. K., and Silva, A. J. (1998). Autophosphorylation at Thr286 of the alpha calcium-calmodulin kinase II in LTP and learning. Science 279, 870-3.

Gomez, M., De Castro, E., Guarin, E., Sasakura, H., Kuhara, A., Mori, I., Bartfai, T., Bargmann, C. I., and Nef, P. (2001). Ca(2+) Signaling via the Neuronal Calcium Sensor-1 Regulates Associative Learning and Memory in C. elegans. Neuron 30, 241-8.

Gray, J. A. (1982). The Neuropsychology of Anxiety: an enquiry into the function of the septo-hippocampal system." (Oxford: Oxford University press).

Hedgecock, E. M., and Russell, R. L. (1975). Normal and mutant thermotaxis in the nematode Caenorhabditis elegans. Proc Natl Acad Sci USA 72, 4061-5.

Hendricks, K. B., Wang, B. Q., Schnieders, E. A., and Thorner, J. (1999). Yeast homologue of neuronal frequenin is a regulator of phosphatidylinositol-4-OH kinase. Nat Cell Biol 1, 234-41.

Higgins, G. A., Grottick, A. J., Ballard, T. M., Richards, J. G., Messer, J., Takeshima, H., Pauly-Evers, M., Jenck, F., Adam, G., and Wichmann, J. (2001). Influence of the selective ORL1 receptor agonist, Ro64-6198, on rodent neurological function. Neuropharmacology 41, 97-107.

Hobert, O., Mori, I., Yamashita, Y., Honda, H., Ohshima, Y., Liu, Y., and Ruvkun, G. (1997). Regulation of interneuron function in the C. elegans thermoregulatory pathway by the ttx-3 LIM homeobox gene. Neuron 19, 345-57.

Hogan, B., Beddington, R., Costantini, F. and Lacy, E. (1994). Manipulating the Mouse Embryo: A Laboratory Manual., C. S. H. L. Press, ed. (Cold Spring Harbor, N.Y.

Iacovelli, L., Sallese, M., Mariggio, S., and de Blasi, A. (1999). Regulation of G-protein-coupled receptor kinase subtypes by calcium sensor proteins. Faseb J 13, 1-8.

Jia, Z., Agopyan, N., Miu, P., Xiong, Z., Henderson, J., Gerlai, R., Taverna, F. A., Velumian, A., MacDonald, J., Carlen, P., Abramow-Newerly, W., and Roder, J. (1996). Enhanced LTP in mice deficient in the AMPA receptor GluR2. Neuron 17, 945-56.

Kelley, K. A., Friedrich, V. L., Jr., Sonshine, A., Hu, Y., Lax, J., Li, J., Drinkwater, D., Dressier, H., and Herrup, K. (1994). Expression of Thy-1/lacZ fusion genes in the CNS of transgenic mice. Brain Res Mol Brain Res 24, 261-74.

Kew, J. N., Koester, A., Moreau, J. L., Jenck, F., Ouagazzal, A. M., Mutel, V., Richards, J. G., Trube, G., Fischer, G., Montkowski, A., Hundt, W., Reinscheid, R. K., Pauly-Evers, M., Kemp, J. A., and Bluethmann, H. (2000). Functional consequences of reduction in NMDA receptor glycine affinity in mice carrying targeted point mutations in the glycine binding site. J Neurosci 20, 4037-49.

Kim, J. J., and Baxter, M. G. (2001). Multiple brain-memory systems: the whole does not equal the sum of its parts. Trends Neurosci 24, 324-30.

Koster, A., Montkowski, A., Schulz, S., Stube, E. M., Knaudt, K., Jenck, F., Moreau, J. L., Nothacker, H. P., Civelli, O., and Reinscheid, R. K. (1999). Targeted disruption of the orphanin FQ/nociceptin gene increases stress susceptibility and impairs stress adaptation in mice. Proc Natl Acad Sci USA 96, 10444-9.

Madani, R., Hulo, S., Toni, N., Madani, H., Steimer, T., Muller, D., and Vassalli, J. D. (1999). Enhanced hippocampal long-term potentiation and learning by increased neuronal expression of tissue-type plasminogen activator in transgenic mice. Embo J 18, 3007-12.

Mallart, A., and Martin, A. R. (1968). The relation between quantum content and facilitation at the neuromuscular junction of the frog. J Physiol 196, 593-604.

Malleret, G., Haditsch, U., Genoux, D., Jones, M. W., Bliss, T. V., Vanhoose, A. M., Weitlauf, C., Kandel, E. R., Winder, D. G., and Mansuy, I. M. (2001). Inducible and reversible enhancement of learning, memory, and long-term potentiation by genetic inhibition of calcineurin. Cell 104, 675-86.

Martin, A. R. (1976). The effect of membrane capacitance on non-linear summation of synaptic potentials. J Theor Biol 59,179-87.

Martone, M. E., Edelmann, V. M., Ellisman, M. H., and Nef, P. (1999). Cellular and subcellular distribution of the calcium-binding protein NCS-1 in the central nervous system of the rat. Cell Tissue Res 295, 395-407.

Maruyama, K., Mikawa, T., and Ebashi, S. (1984). Detection of calcium binding proteins by 45Ca autoradiography on nitrocellulose membrane after sodium dodecyl sulfate gel electrophoresis. J Biochem (Tokyo) 95, 511-9.

Mayford, M., Bach, M. E., Huang, Y. Y., Wang, L., Hawkins, R. D., and Kandel, E. R. (1996). Control of memory formation through regulated expression of a CaMKII transgene. Science 274, 1678-83.

McFerran, B. W., Graham, M. E., and Burgoyne, R. D. (1998). Neuronal Ca2+ sensor 1, the mammalian homologue of frequenin, is expressed in chromaffin and PC12 cells and regulates neurosecretion from dense-core granules. J Biol Chem 273, 22768-72.

Mello, C. C., Kramer, J. M., Stinchcomb, D., and Ambros, V. (1991). Efficient gene transfer in C. elegans: extrachromosomal maintenance and integration of transforming sequences. Embo J 10, 3959-70.

Migaud, M., Chariesworth, P., Dempster, M., Webster, L. C., Watabe, A. M., Makhinson, M., He, Y., Ramsay, M. F., Morris, R. G., Morrison, J. H., O'Dell, T. J., and Grant, S. G. (1999). Enhanced long-term potentiation and impaired learning in mice with mutant postsynaptic density-95 protein. Proc Natl Acad Sci USA 96, 435-40.

Milner, B., Squire, L. R., and Kandel, E. R. (1998). Cognitive neuroscience and the study of memory. Neuron 20, 445-68.

Mori, I. (1999). Genetics of chemotaxis and thermotaxis in the nematode Caenorhabditis elegans. Annu Rev Genet 33, 399-422.

Mori, I., and Ohshima, Y. (1995). Neural regulation of thermotaxis in Caenorhabditis elegans. Nature 376, 344-8.

Muller, D., Wang, C., Skibo, G., Toni, N., Cremer, H., Calaora, V., Rougon, G., and Kiss, J. Z. (1996). PSA-NCAM is required for activity-induced synaptic plasticity. Neuron 17, 413-22.

Nef, S., Fiumelli, H., de Castro, E., Raes, M. B., and Nef, P. (1995). Identification of neuronal calcium sensor (NCS-1) possibly involved in the regulation of receptor phosphorylation. J Recept Signal Transduct Res 15, 365-78.

Nef, P. (1996). Neuron specific calcium sensors: The NCS subfamily. In Guidebook to the calcium-binding proteins, M. R. Celio, ed. (Oxford: Sambrook and Tooze Publication), pp. 94-98, 112-114.

Nicoll, R. A., and Malenka, R. C. (1995). Contrasting properties of two forms of long-term potentiation in the hippocampus. Nature 377, 115-8.

Olafsson, P., Wang, T., and Lu, B. (1995). Molecular cloning and functional characterization of the *Xenopus* Ca(2+)-binding protein frequenin. Proc Natl Acad Sci USA 92, 8001-5.

Paterlini, M., Revilla, V., Grant, A. L., and Wisden, W. (2000). Expression of the neuronal calcium sensor protein family in the rat brain. Neuroscience 99, 205-16.

Plasterk, R. H. (1995). Reverse genetics: from gene sequence to mutant worm. Methods Cell Biol 48, 59-80.

Picciotto, M. R., and Wickman, K. (1998). Using knockout and transgenic mice to study neurophysiology and behavior. Physiol Rev 78, 1131-63.

Pongs, O., Lindemeier, J., Zhu, X. R., Theil, T., Engelkamp, D., Krah-Jentgens, I., Lambrecht, H. G., Koch, K. W., Schwemer, J., Rivosecchi, R., and et al. (1993). Frequenin—a novel calcium-binding protein that modulates synaptic efficacy in the *Drosophila* nervous system. Neuron 11, 15-28.

Poulain, C., Ferrus, A., and Mallart, A. (1994). Modulation of type A K+ current in *Drosophila* larval muscle by internal Ca2+; effects of the overexpression of frequenin. Pflugers Arch 427, 71-9.

Putkey, J. A., Sweeney, H. L., and Campbell, S. T. (1989). Site-directed mutation of the trigger calcium-binding sites in cardiac troponin C. J Biol Chem 264, 12370-8.

Redman, R. S., and Silinsky, E. M. (1994). ATP released together with acetylcholine as the mediator of neuromuscular depression at frog motor nerve endings. J Physiol 477, 117-27.

Rivosecchi, R., Pongs, O., Theil, T., and Mallart, A. (1994). Implication of frequenin in the facilitation of transmitter release in *Drosophila*. J Physiol 474, 223-32.

Rossi-Arnaud, C., and Ammassari-Teule, M. (1998). What do comparative studies of inbred mice add to current investigations on the neural basis of spatial behaviors? Exp Brain Res 123, 36-44.

Routtenberg, A., Cantallops, I., Zaffuto, S., Serrano, P., and Namgung, U. (2000). Enhanced learning after genetic overexpression of a brain growth protein. Proc Natl Acad Sci USA 97, 7657-62.

Schaad, N. C., De Castro, E., Nef, S., Hegi, S., Hinrichsen, R., Martone, M. E., Ellisman, M. H., Sikkink, R., Rusnak, F., Sygush, J., and Nef, P. (1996). Direct modulation of calmodulin targets by the neuronal calcium sensor NCS-1. Proc Natl Acad Sci USA 93, 9253-8.

Schaeren-Wiemers, N., and Gerfin-Moser, A. (1993). A single protocol to detect transcripts of various types and expression levels in neural tissue and cultured cells: in situ hybridization using digoxigenin-labelled cRNA probes. Histochemistry 100, 431-40.

Schnurra, I., Bernstein, H. G., Riederer, P., and Braunewell, K. H. (2001). The Neuronal Calcium Sensor Protein VILIP-1 Is Associated with Amyloid Plaques and Extracellular Tangles in Alzheimer's Disease and Promotes Cell Death and Tau Phosphorylation in Vitro: A Link between Calcium Sensors and Alzheimer's Disease? Neurobiol Dis 8, 900-9.

Silva, A. J., Paylor, R., Wehner, J. M., and Tonegawa, S. (1992). Impaired spatial learning in alpha-calcium-calmodulin kinase 11 mutant mice. Science 257, 206-11.

Silva, A. J., Stevens, C. F., Tonegawa, S., and Wang, Y. (1992). Deficient hippocampal long-term potentiation in alpha-calcium-calmodulin kinase II mutant mice. Science 257, 201-6.

Tang, Y. P., Shimizu, E., Dube, G. R., Rampon, C., Kerchner, G. A., Zhuo, M., Liu, G., and Tsien, J. Z. (1999). Genetic enhancement of learning and memory in mice. Nature 401, 63-9.

Tsien, J. Z., Chen, D. F., Gerber, D., Tom, C., Mercer, E. H., Anderson, D. J., Mayford, M., Kandel, E. R., and Tonegawa, S. (1996). Subregion- and cell type-restricted gene knockout in mouse brain. Cell 87, 1317-26.

Tsien, J. Z., Huerta, P. T., and Tonegawa, S. (1996). The essential role of hippocampal CA1 NMDA receptor-dependent synaptic plasticity in spatial memory. Cell 87, 1327-38.

Uetani, N., Kato, K., Ogura, H., Mizuno, K., Kawano, K., Mikoshiba, K., Yakura, H., Asano, M., and Iwakura, Y. (2000). Impaired learning with enhanced hippocampal long-term potentiation in PTPdelta-deficient mice. Embo J 19, 2775-85.

Wei, W. Z., and Xie, C. W. (1999). Orphanin FQ suppresses NMDA receptor-dependent long-term depression and depotentiation in hippocampal dentate gyrus. Learn Mem 6, 467-77.

Weiss, J. L., and Burgoyne, R. D. (2001). Voltage-independent inhibition of P/Q-type Ca2+ channels in adrenal chromaffin cells via a neuronal Ca2+ sensor-1-dependent pathway involves Src-family tyrosine kinase. J Biol Chem 2, 2.

Wittenburg, N., and Baumeister, R. (1999). Thermal avoidance in *Caenorhabditis elegans*: an approach to the study of nociception. Proc Natl Acad Sci USA 96, 10477-82.

Yazejian, B., Sun, X. P., and Grinnell, A. D. (2000). Tracking presynaptic Ca2+ dynamics during neurotransmitter release with Ca2+-activated K+ channels. Nat Neurosci 3, 566-71.

Yu, S., Avery, L., Baude, E., and Garbers, D. L. (1997). Guanylyl cyclase expression in specific sensory neurons: a new family of chemosensory receptors. Proc Natl Acad Sci USA 94, 3384-7.

Zamanillo, D., Sprengel, R., Hvalby, O., Jensen, V., Burnashev, N., Rozov, A., Kaiser, K. M., Koster, H. J., Borchardt, T., Worley, P., Lubke, J., Frotscher, M., Kelly, P. H., Sommer, B., Andersen, P., Seeburg, P. H., and Sakmann, B. (1999). Importance of AMPA receptors for hippocampal synaptic plasticity but not for spatial learning. Science 284, 1805-11.

Zhao, X., Vamai, P., Tuymetova, G., Balla, A., Toth, Z. E., Oker-Blom, C., Roder, J., Jeromin, A., and Balla, T. (2001). Interaction of neuronal calcium sensor-1(NCS-1) with phosphatidylinositol 4-kinase beta stimulates lipid kinase activity and affects membrane trafficking in COS-7 cells. J Biol Chem 28, 28.

What is claimed is:

1. A method for determining whether an agent is an agonist of the neuron-specific calcium sensor-1 (NCS-1), for consideration of an agonist of NCS-1 as a drug candidate for therapy of a behavioral disorder or for improving learning and/or memory of a subject, said method comprising the steps of:
 (a) contacting a non-human animal selected from the group consisting of NCS-1 transgenic *C. elegans* that overexpress NCS-1 and transgenic mice that overexpress chick NCS-1 under control of the Thy1 promotor with an exogenous agent to be screened in the presence of calcium; and
 (b) determining NCS-1 activity of said non-human animal, wherein an increase in NCS-1 activity compared with a corresponding control animal is indicative of an agent which is an agonist of NCS-1.

2. The method of claim 1, wherein said NCS-1 activity is calcium binding or a change of conformation or function.

3. The method of claim 1, wherein said transgenic non-human animal displays an increase in NCS-1 associated behavior as compared to the corresponding control animal.

4. The method of claim 3, wherein said transgenic non-human animal is *C. elegans* and said behavior is isothermal tracking (IT).

5. The method of claim 3, wherein said transgenic non-human animal is a mouse and said behavior is learning and memory performance in the Morris water maze and active avoidance tasks.

* * * * *